US005491086A

United States Patent [19]
Gelfand et al.

[11] Patent Number: 5,491,086
[45] Date of Patent: Feb. 13, 1996

[54] PURIFIED THERMOSTABLE NUCLEIC ACID POLYMERASE AND DNA CODING SEQUENCES FROM PYRODICTIUM SPECIES

[75] Inventors: David H. Gelfand, Oakland; Alice M. Wang, Lafayette, both of Calif.

[73] Assignee: Hoffmann-La Roche Inc., Nutley, N.J.

[21] Appl. No.: 62,368

[22] Filed: May 14, 1993

[51] Int. Cl.$^6$ ............... C12N 9/12; C12N 15/54; C12N 15/74; C12N 1/19

[52] U.S. Cl. ............... 435/194; 435/252.3; 435/320.1; 930/240; 536/23.2; 536/23.7

[58] Field of Search ............... 435/193, 194, 435/172.3, 320.1, 252.3; 536/23.2, 23.7; 930/240

[56] References Cited

U.S. PATENT DOCUMENTS

| | | | |
|---|---|---|---|
| 5,210,015 | 5/1993 | Gelfand et al. | 435/196 |
| 5,210,036 | 5/1993 | Comb et al. | 435/194 |
| 5,223,414 | 6/1993 | Zarling et al. | 435/91 |
| 5,242,817 | 9/1993 | Kelly et al. | 435/212 |
| 5,322,785 | 6/1994 | Comb et al. | 435/194 |
| 5,338,671 | 8/1994 | Scalice et al. | 435/91.2 |
| 5,352,778 | 10/1994 | Comb et al. | 536/23.2 |
| 5,407,800 | 4/1995 | Gelfand et al. | 435/6 |

FOREIGN PATENT DOCUMENTS

| | | |
|---|---|---|
| 373962 | 6/1990 | European Pat. Off. . |
| 0455430 | 11/1991 | European Pat. Off. . |
| 9209689 | 6/1992 | WIPO . |

OTHER PUBLICATIONS

Mathur, "Applications of Thermostable DNA Polymerases in Molecular Biology", pp. 189–206 *Biocatalysis at Extreme Temperatures*, (ACS, Wash D.C., 1992).

Sturm et al, pp. 51–66 in *Biochemical Engineering V*, NYAS (NY) 1987.

Pley et al, *System Appl. Microbiol.* 14:245–253 (1991).

Lundberg et al, "High–Fidelity Amplification Using a Thermostable DNA Polymerase . . . from *Pyrococcus furiosus*"108:1–6 (1991).

Phipps et al, "A Novel ATPase Complex . . . of Thermophilic Archaebacteria", *The Embo J.* 10(7): 1711–1722 (Jul. 1991).

Wheelis et al "On the Nature of Global Classification" *PNAS* 89:2930–2934 (Apr. 1992).

Mathur et al, "The DNA Polymerase Gene from . . . *Pyrococcus furiosus* . . . ", *Nuc. Acids Res.* 19(24): 6952 (Dec. 1991).

Fiala et al "*Pyrococcus furiosus* Sp. Nov. Represents a Novel Genus of Marine Heterotrophic Archaebacteria . . . " *Arch. Microbio.* 14:56–61 (1986).

Perler et al "Intervening Sequences in an Archaea DNA Polymerase Gene", *PNAS* 89:5577–5581 (Jun. 1992).

Lawyer et al, "Isolation, Characterization, and Expression in *Escherchia coli* of the DNA Polymerase Gene from *Thermia aquaticus*", *J. Biol. Chem.* 264(11): 6427–6437 (Apr. 1989).

*Primary Examiner*—Steven G. Walsh
*Attorney, Agent, or Firm*—George M. Gould; Stacey R. Sias; Douglas A. Petry

[57] ABSTRACT

Recombinant DNA sequences encoding the DNA polymerase activity of Pyrodictium species can be used to construct recombinant vectors and transformed host cells for production of the activity. Pyrodictium enzymes for catalyzing 3'→5' exonuclease activity, i.e., proofreading enzymes, are also provided. The Pyrodictium enzymes are useful in DNA amplification procedures and are not irreversibly inactivated by exposure to 100° C. in a polymerase chain reaction.

20 Claims, No Drawings

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
( A ) LENGTH: 2430 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
ATGCCAGAAG  CTATAGAGTT  CGTGCTCCTT  GATTCAAGCT  ACGAGATTGT  AGGGAAAGAG     60
CCGGTAATCA  TACTATGGGG  TGTAACGCTA  GACGGTAAAC  GCATAGTCCT  ACTTGATAGG    120
AGGTTTAGGC  CCTACTTCTA  TGCACTCATA  TCCCGCGACT  ACGAAGGTAA  GGCCGAGGAG    180
GTAGTAGCTG  CTATTAGAAG  GCTAAGTATG  GCAAAGAGCC  CCATAATAGA  AGCAAAGGTG    240
GTTAGTAAGA  AGTACTTCGG  AAGGCCCCGT  AAAGCAGTCA  AAGTAACGAC  AGTTATACCC    300
GAATCTGTCA  GAGAATATAG  AGAGGCTGTA  AAAAAGCTGG  AAGGCGTGGA  AGACTCTCTA    360
GAAGCAGACA  TAAGGTTCGC  GATGAGGTAT  CTAATCGACA  AGAAGCTCTA  CCCGTTCACA    420
GCATACCGTG  TCAGAGCCGA  GAACGCTGGA  CGCAGCCCTG  GTTTCCGTGT  AGACTCGGTA    480
TACACTATAG  TTGAGGACCC  AGAGCCTATT  GCCGACATAA  CTAGTATAGA  TATACCAGAG    540
ATGCGTGTGC  TCGCGTTCGA  CATAGAGGTC  TACAGTAAGA  GAGGAAGCCC  TAACCCGTCC    600
CGCGACCCGG  TCATAATAAT  CTCGATAAAG  GACAGCAAGG  GGAACGAGAA  GCTACTAGAA    660
GCCAATAACT  ACGACGACAG  AAACGTGCTA  CGGGAATTTA  TAGAGTACAT  ACGCTCCTTT    720
GACCCAGACA  TAATAGTAGG  CTACAATAGC  AACAATTTTG  ACTGGCCATA  CCTTATAGAA    780
CGTGCACACA  GAATAGGAGT  AAAGCTCGAC  GTGACAAGGC  GTGTTGGCGC  AGAGCCAAGT    840
ATGAGCGTCT  ATGGACATGT  CTCAGTGCAG  GGTAGGCTAA  ACGTAGACCT  CTACAACTAC    900
GTGGAGGAAA  TGCATGAGAT  AAAGGTAAAG  ACGCTCGAGG  AGGTCGCCGA  ATACCTAGGC    960
GTTATGCGCA  AGAGCGAGCG  CGTACTAATA  GAATGGTGGC  GGATCCAGA   TTACTGGGAC   1020
GACGAGAAGA  AACGGCCGCT  ACTGAAGCGT  TATGCCCTCG  ACGATGTGAG  AGCCACCTAC   1080
GGCCTCGCCG  AGAAGATACT  CCCATTCGCA  ATACAGCTTT  CGACAGTAAC  CGGTGTTCCT   1140
TTAGACCAAG  TCGGGGCTAT  GGGCGTAGGT  TTCCGTCTAG  AATGGTACCT  TATGAGAGCA   1200
GCGCATGATA  TGAACGAGCT  TGTCCCCAAC  CGTGTCAAGC  GGCGCGAAGA  GAGCTACAAG   1260
GGAGCAGTAG  TACTAAAGCC  CCTAAAGGGT  GTCCATGAGA  ACGTAGTAGT  GCTCGACTTT   1320
AGCTCAATGT  ACCCCAACAT  AATGATAAAG  TACAATGTGG  GCCCTGACAC  GATAATTGAC   1380
```

```
GACCCCTCAG AGTGCGAGAA GTACAGTGGA TGCTACGTAG CCCCCGAAGT CGGGCACATG    1440

TTTAGGCGCT CGCCCTCCGG CTTCTTTAAG ACCGTGCTTG AGAACCTCAT AGCGCTGCGT    1500

AAGCAAGTAC GTGAAAAGAT GAAGGAGTTC CCCCCAGATA GCCCAGAATA CCGGATATAC    1560

GATGAACGCC AGAAGGCACT CAAGGTGCTA GCCAACGCTA GCTACGGCTA CATGGGATGG    1620

GTGCACGCTC GCTGGTACTG TAAACGCTGC GCAGAGGCTG TAACAGCCTG GGGCCGTAAC    1680

CTGATACTCT CAGCAATAGA ATATGCTAGG AAGCTCGGCC TCAAAGTAAT ATACGGAGAC    1740

ACGGACTCCC TATTCGTAAC CTATGATATC GAGAAGGTAA AGAAGCTAAT AGAATTCGTC    1800

GAGAAACAGC TAGGCTTCGA GATAAAGATA GACAAGGTAT ACAAAGAGT  GTTCTTTACC    1860

GAGGCAAAGA AGCGCTACGT GGGCCTCCTC GAGGACGGGC GTATGGACAT AGTAGGCTTT    1920

GAGGCTGTTA GAGGCGACTG GTGTGAGCTA GCTAAGAGG  TGCAAGAGAA AGTAGCAGAG    1980

ATAATACTGA AGACGGGAGA CATAAATAGA GCCATAAGCT ACATAAGAGA GGTCGTGAGA    2040

AAGCTAAGAG AAGGCAAGAT ACCCATAACA AAGCTCGTAA TATGGAAGAC CTTGACAAAG    2100

AGAATCGAGG AATACGAGCA CGAGGCGCCG CACGTTACTG CAGCACGGCG TATGAAAGAA    2160

GCAGGCTACG ATGTGGCACC GGGAGACAAG ATAGGCTACA TCATAGTTAA AGGACATGGC    2220

AGTATATCGA GTCGTGCCTA CCCGTACTTT ATGGTAGACT CGTCTAAGGT TGACACAGAG    2280

TACTACATAG ACCACCAGAT AGTACCAGCA GCAATGAGGA TACTCTCATA CTTCGGGGTC    2340

ACAGAGAAGC AGCTTAAGGC AGCATCATCT GGGCATAGGA GTCTCTTCGA CTTCTTCGCG    2400

GCAAAGAAGT AGCCCCGGCT CTCCAAACTA                                     2430
```

( 2 ) INFORMATION FOR SEQ ID NO:2:

( i ) SEQUENCE CHARACTERISTICS:
( A ) LENGTH: 803 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

```
Met Pro Glu Ala Ile Glu Phe Val Leu Leu Asp Ser Ser Tyr Glu Ile
 1               5                  10                  15

Val Gly Lys Glu Pro Val Ile Ile Leu Trp Gly Val Thr Leu Asp Gly
            20                  25                  30

Lys Arg Ile Val Leu Leu Asp Arg Arg Phe Arg Pro Tyr Phe Tyr Ala
        35                  40                  45

Leu Ile Ser Arg Asp Tyr Glu Gly Lys Ala Glu Glu Val Val Ala Ala
    50                  55                  60

Ile Arg Arg Leu Ser Met Ala Lys Ser Pro Ile Ile Glu Ala Lys Val
65                  70                  75                  80

Val Ser Lys Lys Tyr Phe Gly Arg Pro Arg Lys Ala Val Lys Val Thr
                85                  90                  95

Thr Val Ile Pro Glu Ser Val Arg Glu Tyr Arg Glu Ala Val Lys Lys
            100                 105                 110

Leu Glu Gly Val Glu Asp Ser Leu Glu Ala Asp Ile Arg Phe Ala Met
        115                 120                 125

Arg Tyr Leu Ile Asp Lys Lys Leu Tyr Pro Phe Thr Ala Tyr Arg Val
    130                 135                 140

Arg Ala Glu Asn Ala Gly Arg Ser Pro Gly Phe Arg Val Asp Ser Val
145                 150                 155                 160
```

```
Tyr  Thr  Ile  Val  Glu  Asp  Pro  Glu  Pro  Ile  Ala  Asp  Ile  Thr  Ser  Ile
               165                 170                      175

Asp  Ile  Pro  Glu  Met  Arg  Val  Leu  Ala  Phe  Asp  Ile  Glu  Val  Tyr  Ser
               180                 185                      190

Lys  Arg  Gly  Ser  Pro  Asn  Pro  Ser  Arg  Asp  Pro  Val  Ile  Ile  Ile  Ser
               195                 200                      205

Ile  Lys  Asp  Ser  Lys  Gly  Asn  Glu  Lys  Leu  Leu  Glu  Ala  Asn  Asn  Tyr
          210                 215                      220

Asp  Asp  Arg  Asn  Val  Leu  Arg  Glu  Phe  Ile  Glu  Tyr  Ile  Arg  Ser  Phe
225                      230                 235                           240

Asp  Pro  Asp  Ile  Ile  Val  Gly  Tyr  Asn  Ser  Asn  Phe  Asp  Trp  Pro
               245                 250                      255

Tyr  Leu  Ile  Glu  Arg  Ala  His  Arg  Ile  Gly  Val  Lys  Leu  Asp  Val  Thr
               260                 265                      270

Arg  Arg  Val  Gly  Ala  Glu  Pro  Ser  Met  Ser  Val  Tyr  Gly  His  Val  Ser
          275                 280                      285

Val  Gln  Gly  Arg  Leu  Asn  Val  Asp  Leu  Tyr  Asn  Tyr  Val  Glu  Glu  Met
     290                 295                      300

His  Glu  Ile  Lys  Val  Lys  Thr  Leu  Glu  Glu  Val  Ala  Glu  Tyr  Leu  Gly
305                      310                 315                           320

Val  Met  Arg  Lys  Ser  Glu  Arg  Val  Leu  Ile  Glu  Trp  Trp  Arg  Ile  Pro
               325                 330                      335

Asp  Tyr  Trp  Asp  Asp  Glu  Lys  Lys  Arg  Pro  Leu  Leu  Lys  Arg  Tyr  Ala
               340                 345                      350

Leu  Asp  Asp  Val  Arg  Ala  Thr  Tyr  Gly  Leu  Ala  Glu  Lys  Ile  Leu  Pro
          355                 360                      365

Phe  Ala  Ile  Gln  Leu  Ser  Thr  Val  Thr  Gly  Val  Pro  Leu  Asp  Gln  Val
370                      375                 380

Gly  Ala  Met  Gly  Val  Gly  Phe  Arg  Leu  Glu  Trp  Tyr  Leu  Met  Arg  Ala
385                      390                 395                           400

Ala  His  Asp  Met  Asn  Glu  Leu  Val  Pro  Asn  Arg  Val  Lys  Arg  Arg  Glu
               405                 410                      415

Glu  Ser  Tyr  Lys  Gly  Ala  Val  Val  Leu  Lys  Pro  Leu  Lys  Gly  Val  His
               420                 425                      430

Glu  Asn  Val  Val  Val  Leu  Asp  Phe  Ser  Ser  Met  Tyr  Pro  Asn  Ile  Met
          435                 440                      445

Ile  Lys  Tyr  Asn  Val  Gly  Pro  Asp  Thr  Ile  Ile  Asp  Asp  Pro  Ser  Glu
     450                 455                      460

Cys  Glu  Lys  Tyr  Ser  Gly  Cys  Tyr  Val  Ala  Pro  Glu  Val  Gly  His  Met
465                      470                 475                           480

Phe  Arg  Arg  Ser  Pro  Ser  Gly  Phe  Phe  Lys  Thr  Val  Leu  Glu  Asn  Leu
               485                 490                      495

Ile  Ala  Leu  Arg  Lys  Gln  Val  Arg  Glu  Lys  Met  Lys  Glu  Phe  Pro  Pro
               500                 505                      510

Asp  Ser  Pro  Glu  Tyr  Arg  Ile  Tyr  Asp  Glu  Arg  Gln  Lys  Ala  Leu  Lys
               515                 520                      525

Val  Leu  Ala  Asn  Ala  Ser  Tyr  Gly  Tyr  Met  Gly  Trp  Val  His  Ala  Arg
          530                 535                      540

Trp  Tyr  Cys  Lys  Arg  Cys  Ala  Glu  Ala  Val  Thr  Ala  Trp  Gly  Arg  Asn
545                      550                 555                           560

Leu  Ile  Leu  Ser  Ala  Ile  Glu  Tyr  Ala  Arg  Lys  Leu  Gly  Leu  Lys  Val
               565                 570                      575

Ile  Tyr  Gly  Asp  Thr  Asp  Ser  Leu  Phe  Val  Thr  Tyr  Asp  Ile  Glu  Lys
               580                 585                      590
```

```
Val  Lys  Lys  Leu  Ile  Glu  Phe  Val  Glu  Lys  Gln  Leu  Gly  Phe  Glu  Ile
          595                      600                     605

Lys  Ile  Asp  Lys  Val  Tyr  Lys  Arg  Val  Phe  Phe  Thr  Glu  Ala  Lys  Lys
          610                      615                     620

Arg  Tyr  Val  Gly  Leu  Leu  Glu  Asp  Gly  Arg  Met  Asp  Ile  Val  Gly  Phe
625                      630                     635                      640

Glu  Ala  Val  Arg  Gly  Asp  Trp  Cys  Glu  Leu  Ala  Lys  Glu  Val  Gln  Glu
               645                      650                     655

Lys  Val  Ala  Glu  Ile  Ile  Leu  Lys  Thr  Gly  Asp  Ile  Asn  Arg  Ala  Ile
               660                      665                     670

Ser  Tyr  Ile  Arg  Glu  Val  Val  Arg  Lys  Leu  Arg  Glu  Gly  Lys  Ile  Pro
          675                      680                     685

Ile  Thr  Lys  Leu  Val  Ile  Trp  Lys  Thr  Leu  Thr  Lys  Arg  Ile  Glu  Glu
     690                      695                     700

Tyr  Glu  His  Glu  Ala  Pro  His  Val  Thr  Ala  Ala  Arg  Arg  Met  Lys  Glu
705                      710                     715                      720

Ala  Gly  Tyr  Asp  Val  Ala  Pro  Gly  Asp  Lys  Ile  Gly  Tyr  Ile  Ile  Val
               725                      730                     735

Lys  Gly  His  Gly  Ser  Ile  Ser  Ser  Arg  Ala  Tyr  Pro  Tyr  Phe  Met  Val
               740                      745                     750

Asp  Ser  Ser  Lys  Val  Asp  Thr  Glu  Tyr  Tyr  Ile  Asp  His  Gln  Ile  Val
          755                      760                     765

Pro  Ala  Ala  Met  Arg  Ile  Leu  Ser  Tyr  Phe  Gly  Val  Thr  Glu  Lys  Gln
     770                      775                     780

Leu  Lys  Ala  Ala  Ser  Ser  Gly  His  Arg  Ser  Leu  Phe  Asp  Phe  Phe  Ala
785                      790                     795                      800

Ala  Lys  Lys
```

( 2 ) INFORMATION FOR SEQ ID NO:3:

( i ) SEQUENCE CHARACTERISTICS:
        ( A ) LENGTH: 2430 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATGACAGAGA  CTATAGAGTT  CGTGCTGCTA  GACTCTAGCT  ACGAGATACT  GGGGAAGGAG   60
CCGGTAGTAA  TCCTCTGGGG  GATAACGCTT  GACGGTAAAC  GTGTCGTGCT  TCTAGACCAC  120
CGCTTCCGCC  CCTACTTCTA  CGCCCTCATA  GCCCGGGGCT  ATGAGGATAT  GGTGGAGGAG  180
ATAGCAGCTT  CCATAAGGAG  GCTTAGTGTG  GTCAAGAGTC  CGATAATAGA  TGCCAAGCCT  240
CTTGATAAGA  GGTACTTCGG  CAGGCCCCGT  AAGGCGGTGA  AGATTACCAC  TATGATACCC  300
GAGTCTGTTA  GACACTACCG  CGAGGCGGTG  AAGAAGATAG  AGGGTGTGGA  GGACTCCCTC  360
GAGGCAGATA  TAAGGTTTGC  AATGAGATAT  CTGATAGATA  AGAGGCTCTA  CCCGTTCACG  420
GTTTACCGGA  TCCCCGTAGA  GGATGCGGGC  CGCAATCCAG  GCTTCCGTGT  TGACCGTGTC  480
TACAAGGTTG  CTGGCGACCC  GGAGCCCCTA  GCGGATATAA  CGCGGATCGA  CCTTCCCCCG  540
ATGAGGCTGG  TAGCTTTTGA  TATAGAGGTG  TATAGCAGGA  GGGGGAGCCC  TAACCCTGCA  600
AGGGATCCAG  TGATAATAGT  GTCGCTGAGG  GACAGCGAGG  GCAAGGAGAG  GCTCATAGAA  660
GCTGAAGGCC  ATGACGACAG  GAGGGTTCTG  AGGGAGTTCG  TAGAGTACGT  GAGAGCCTTC  720
GACCCCGACA  TAATAGTGGG  CTATAACAGT  AACCACTTCG  ACTGGCCCTA  CCTAATGGAG  780
```

| | | | | | |
|---|---|---|---|---|---|
| CGCGCCCGTA | GGCTCGGGAT | TAACCTCGAC | GTTACACGCC | GTGTGGGGGC | AGAGCCCACC | 840 |
| ACCAGCGTCT | ACGGCCACGT | CTCGGTGCAG | GGTAGGCTGA | ACGTGGACCT | CTACGACTAT | 900 |
| GCCGAGGAGA | TGCCGGAGAT | AAAGATGAAG | ACGCTTGAGG | AGGTAGCGGA | GTACCTAGGC | 960 |
| GTTATGAAGA | AGAGCGAGCG | TGTGATAATA | GAGTGGTGGA | GGATACCCGA | GTACTGGGAT | 1020 |
| GACGAGAAGA | AGAGGCAGCT | GCTAGAGCGC | TACGCGCTCG | ACGATGTGAG | GGCTACCTAC | 1080 |
| GGCCTCGCGG | AAAAGATGCT | ACCGTTCGCC | ATACAGCTCT | CCACTGTTAC | GGGTGTGCCT | 1140 |
| CTCGACCAGG | TAGGTGCTAT | GGGCGTAGGC | TTCCGCCTAG | AGTGGTATCT | CATGCGTGCA | 1200 |
| GCCTACGATA | TGAACGAGCT | GGTGCCGAAC | CGGGTGGAGA | GGAGGGGGA | GAGCTACAAG | 1260 |
| GGTGCAGTAG | TGTTAAAGCC | TCTCAAGGGA | GTCCATGAGA | ATGTTGTGGT | GCTCGATTTC | 1320 |
| AGTTCCATGT | ACCCGAGCAT | AATGATAAAG | TACAACGTGG | GCCCCGACAC | TATAGTCGAC | 1380 |
| GACCCCTCGG | AGTGCCCAAA | GTACGGCGGC | TGCTATGTAG | CCCCCGAGGT | CGGGCACCGG | 1440 |
| TTCCGTCGCT | CCCCGCCAGG | CTTCTTCAAG | ACCGTGCTCG | AGAACCTACT | GAAGCTACGC | 1500 |
| CGACAGGTAA | AGGAGAAGAT | GAAGGAGTTT | CCGCCTGACA | GCCCCGAGTA | CAGGCTCTAC | 1560 |
| GATGAGCGCC | AGAAGGCGCT | CAAGGTTCTT | GCGAACGCGA | GCTATGGCTA | CATGGGGTGG | 1620 |
| AGCCATGCCC | GCTGGTACTG | CAAACGCTGC | GCCGAGGCTG | TCACAGCCTG | GGGCCGTAAC | 1680 |
| CTTATACTGA | CAGCTATCGA | GTATGCCAGG | AAGCTCGGCC | TAAAGGTTAT | ATATGGAGAC | 1740 |
| ACCGACTCCC | TCTTCGTGGT | CTATGACAAG | GAGAAGGTTG | AGAAGCTGAT | AGAGTTTGTC | 1800 |
| GAGAAGGAGC | TGGGCTTTGA | GATAAAGATA | GACAAGATCT | ACAAGAAAGT | GTTCTTCACG | 1860 |
| GAGGCTAAGA | AGCGCTATGT | AGGTCTCCTC | GAGGACGGAC | GTATAGACAT | CGTGGGCTTT | 1920 |
| GAAGCAGTCC | GCGGCGACTG | GTGCGAGCTG | GCTAAGGAGG | TGCAGGAGAA | GGCGGCTGAG | 1980 |
| ATAGTGTTGA | ATACGGGGAA | CGTGGACAAG | GCTATAAGCT | ACATAAGGGA | GGTAATAAAG | 2040 |
| CAGCTCCGCG | AGGGCAAGGT | GCCAATAACA | AAGCTTATCA | TATGGAAGAC | GCTGAGCAAG | 2100 |
| AGGATAGAGG | AGTACGAGCA | TGACGCGCCT | CATGTGATGG | CTGCACGGCG | TATGAAGGAG | 2160 |
| GCAGGCTACG | AGGTGTCTCC | CGGCGATAAG | GTGGGCTACG | TCATAGTTAA | GGGTAGCGGG | 2220 |
| AGTGTGTCCA | GCAGGGCCTA | CCCCTACTTC | ATGGTTGATC | CATCGACCAT | CGACGTCAAC | 2280 |
| TACTATATTG | ACCACCAGAT | AGTGCCGGCT | GCTCTGAGGA | TACTCTCCTA | CTTCGGAGTC | 2340 |
| ACCGAGAAAC | AGCTCAAGGC | GGCGGCTACG | GTGCAGAGAA | GCCTCTTCGA | CTTCTTCGCC | 2400 |
| TCAAAGAAAT | AGCTCCTCCA | CCCGGCTAGC | | | | 2430 |

( 2 ) INFORMATION FOR SEQ ID NO:4:

( i ) SEQUENCE CHARACTERISTICS:
        ( A ) LENGTH: 803 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
Met  Thr  Glu  Thr  Ile  Glu  Phe  Val  Leu  Leu  Asp  Ser  Ser  Tyr  Glu  Ile
  1                    5                        10                        15

Leu  Gly  Lys  Glu  Pro  Val  Val  Ile  Leu  Trp  Gly  Ile  Thr  Leu  Asp  Gly
              20                        25                        30

Lys  Arg  Val  Val  Leu  Leu  Asp  His  Arg  Phe  Arg  Pro  Tyr  Phe  Tyr  Ala
          35                        40                        45

Leu  Ile  Ala  Arg  Gly  Tyr  Glu  Asp  Met  Val  Glu  Glu  Ile  Ala  Ala  Ser
```

-continued

|   |   |   | 50 |   |   | 55 |   |   |   | 60 |   |   |   |   |
|---|---|---|---|---|---|---|---|---|---|---|---|---|---|---|
| Ile<br>65 | Arg | Arg | Leu | Ser | Val<br>70 | Val | Lys | Ser | Pro | Ile<br>75 | Ile | Asp | Ala | Lys | Pro<br>80 |
| Leu | Asp | Lys | Arg | Tyr<br>85 | Phe | Gly | Arg | Pro | Arg<br>90 | Lys | Ala | Val | Lys | Ile<br>95 | Thr |
| Thr | Met | Ile | Pro<br>100 | Glu | Ser | Val | Arg | His<br>105 | Tyr | Arg | Glu | Ala | Val<br>110 | Lys | Lys |
| Ile | Glu | Gly<br>115 | Val | Glu | Asp | Ser | Leu<br>120 | Glu | Ala | Asp | Ile | Arg<br>125 | Phe | Ala | Met |
| Arg | Tyr<br>130 | Leu | Ile | Asp | Lys | Arg<br>135 | Leu | Tyr | Pro | Phe | Thr<br>140 | Val | Tyr | Arg | Ile |
| Pro<br>145 | Val | Glu | Asp | Ala | Gly<br>150 | Arg | Asn | Pro | Gly | Phe<br>155 | Arg | Val | Asp | Arg | Val<br>160 |
| Tyr | Lys | Val | Ala | Gly<br>165 | Asp | Pro | Glu | Pro | Leu<br>170 | Ala | Asp | Ile | Thr | Arg<br>175 | Ile |
| Asp | Leu | Pro | Pro<br>180 | Met | Arg | Leu | Val | Ala<br>185 | Phe | Asp | Ile | Glu | Val<br>190 | Tyr | Ser |
| Arg | Arg | Gly<br>195 | Ser | Pro | Asn | Pro | Ala<br>200 | Arg | Asp | Pro | Val | Ile<br>205 | Ile | Val | Ser |
| Leu | Arg<br>210 | Asp | Ser | Glu | Gly | Lys<br>215 | Glu | Arg | Leu | Ile | Glu<br>220 | Ala | Glu | Gly | His |
| Asp<br>225 | Asp | Arg | Arg | Val | Leu<br>230 | Arg | Glu | Phe | Val | Glu<br>235 | Tyr | Val | Arg | Ala | Phe<br>240 |
| Asp | Pro | Asp | Ile | Ile<br>245 | Val | Gly | Tyr | Asn | Ser<br>250 | Asn | His | Phe | Asp | Trp<br>255 | Pro |
| Tyr | Leu | Met | Glu<br>260 | Arg | Ala | Arg | Arg | Leu<br>265 | Gly | Ile | Asn | Leu | Asp<br>270 | Val | Thr |
| Arg | Arg | Val<br>275 | Gly | Ala | Glu | Pro | Thr<br>280 | Thr | Ser | Val | Tyr | Gly<br>285 | His | Val | Ser |
| Val | Gln<br>290 | Gly | Arg | Leu | Asn | Val<br>295 | Asp | Leu | Tyr | Asp | Tyr<br>300 | Ala | Glu | Glu | Met |
| Pro<br>305 | Glu | Ile | Lys | Met | Lys<br>310 | Thr | Leu | Glu | Glu | Val<br>315 | Ala | Glu | Tyr | Leu | Gly<br>320 |
| Val | Met | Lys | Lys | Ser<br>325 | Glu | Arg | Val | Ile | Ile<br>330 | Glu | Trp | Trp | Arg | Ile<br>335 | Pro |
| Glu | Tyr | Trp | Asp<br>340 | Asp | Glu | Lys | Lys | Arg<br>345 | Gln | Leu | Leu | Glu | Arg<br>350 | Tyr | Ala |
| Leu | Asp | Asp<br>355 | Val | Arg | Ala | Thr | Tyr<br>360 | Gly | Leu | Ala | Glu | Lys<br>365 | Met | Leu | Pro |
| Phe | Ala<br>370 | Ile | Gln | Leu | Ser | Thr<br>375 | Val | Thr | Gly | Val | Pro<br>380 | Leu | Asp | Gln | Val |
| Gly<br>385 | Ala | Met | Gly | Val | Gly<br>390 | Phe | Arg | Leu | Glu | Trp<br>395 | Tyr | Leu | Met | Arg | Ala<br>400 |
| Ala | Tyr | Asp | Met | Asn<br>405 | Glu | Leu | Val | Pro | Asn<br>410 | Arg | Val | Glu | Arg | Arg<br>415 | Gly |
| Glu | Ser | Tyr | Lys<br>420 | Gly | Ala | Val | Val | Leu<br>425 | Lys | Pro | Leu | Lys | Gly<br>430 | Val | His |
| Glu | Asn | Val<br>435 | Val | Val | Leu | Asp | Phe<br>440 | Ser | Ser | Met | Tyr | Pro<br>445 | Ser | Ile | Met |
| Ile | Lys<br>450 | Tyr | Asn | Val | Gly | Pro<br>455 | Asp | Thr | Ile | Val | Asp<br>460 | Asp | Pro | Ser | Glu |
| Cys<br>465 | Pro | Lys | Tyr | Gly | Gly<br>470 | Cys | Tyr | Val | Ala | Pro<br>475 | Glu | Val | Gly | His | Arg<br>480 |

-continued

```
Phe Arg Arg Ser Pro Pro Gly Phe Phe Lys Thr Val Leu Glu Asn Leu
            485                 490                 495
Leu Lys Leu Arg Arg Gln Val Lys Glu Lys Met Lys Glu Phe Pro Pro
            500                 505                 510
Asp Ser Pro Glu Tyr Arg Leu Tyr Asp Glu Arg Gln Lys Ala Leu Lys
            515                 520                 525
Val Leu Ala Asn Ala Ser Tyr Gly Tyr Met Gly Trp Ser His Ala Arg
        530                 535                 540
Trp Tyr Cys Lys Arg Cys Ala Glu Ala Val Thr Ala Trp Gly Arg Asn
545                     550                 555                 560
Leu Ile Leu Thr Ala Ile Glu Tyr Ala Arg Lys Leu Gly Leu Lys Val
                565                 570                 575
Ile Tyr Gly Asp Thr Asp Ser Leu Phe Val Val Tyr Asp Lys Glu Lys
            580                 585                 590
Val Glu Lys Leu Ile Glu Phe Val Glu Lys Glu Leu Gly Phe Glu Ile
        595                 600                 605
Lys Ile Asp Lys Ile Tyr Lys Lys Val Phe Phe Thr Glu Ala Lys Lys
    610                 615                 620
Arg Tyr Val Gly Leu Leu Glu Asp Gly Arg Ile Asp Ile Val Gly Phe
625                 630                 635                 640
Glu Ala Val Arg Gly Asp Trp Cys Glu Leu Ala Lys Glu Val Gln Glu
                645                 650                 655
Lys Ala Ala Glu Ile Val Leu Asn Thr Gly Asn Val Asp Lys Ala Ile
            660                 665                 670
Ser Tyr Ile Arg Glu Val Ile Lys Gln Leu Arg Glu Gly Lys Val Pro
        675                 680                 685
Ile Thr Lys Leu Ile Ile Trp Lys Thr Leu Ser Lys Arg Ile Glu Glu
690                 695                 700
Tyr Glu His Asp Ala Pro His Val Met Ala Ala Arg Arg Met Lys Glu
705                 710                 715                 720
Ala Gly Tyr Glu Val Ser Pro Gly Asp Lys Val Gly Tyr Val Ile Val
                725                 730                 735
Lys Gly Ser Gly Ser Val Ser Ser Arg Ala Tyr Pro Tyr Phe Met Val
            740                 745                 750
Asp Pro Ser Thr Ile Asp Val Asn Tyr Tyr Ile Asp His Gln Ile Val
        755                 760                 765
Pro Ala Ala Leu Arg Ile Leu Ser Tyr Phe Gly Val Thr Glu Lys Gln
770                 775                 780
Leu Lys Ala Ala Ala Thr Val Gln Arg Ser Leu Phe Asp Phe Phe Ala
785                 790                 795                 800
Ser Lys Lys
```

( 2 ) INFORMATION FOR SEQ ID NO:5:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GGACCCATAT GCCAGAAGCT ATTGAATTCG TGCTCC    36

( 2 ) INFORMATION FOR SEQ ID NO:6:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

```
GGCAGGTACC  ACTAGTTATG  TCGGCAATAG  GCTC                              3 4
```

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
TTAAGGCAGC  ATCATCTGGG  CATAGGAGTC  TCTTCGACTT  CTTCGCGGCA  AAGAAGTAAC    6 0
```

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
CCGGGTTACT  TCTTTGCCGC  GAAGAAGTCG  AAGAGACTCC  TATGCCCAGA  TGATGCTGCC    6 0
```

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GCTTATAGCC  TTGTCCACGT  TC                                            2 2
```

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GGACCATGCA  TGACTGAAAC  TATTGAATTC  GTGCTG                            3 6
```

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:11:

GGAAGGTACC  TGATCATCTA  GAAGCACGAC  ACGTT                              35

( 2 ) INFORMATION FOR SEQ ID NO:12:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:12:

GGAAGCTGAG  CAAGAGGATA  GAGG                                           24

( 2 ) INFORMATION FOR SEQ ID NO:13:

(  i  ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:13:

GGAAGGTACC  TTATTTCTTT  GAGGCGAAGA  AG                                 32

( 2 ) INFORMATION FOR SEQ ID NO:14:

(  i  ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:14:

TTTTTCGAAA  GAAGAAAAAA  CC                                             22

( 2 ) INFORMATION FOR SEQ ID NO:15:

(  i  ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:15:

TCTCATATGC  TTATCGATAC  CC                                             22

( 2 ) INFORMATION FOR SEQ ID NO:16:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:16:

```
CATAAGCTTA TCGATACCCT T                                                          2 1
```

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
AAGCTTATGA CAGAGACTAT AGAGTT                                                     2 6
```

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
GTGGTCTAGA AGCACGACAC GT                                                         2 2
```

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
TATTGCCGAC ATAACTAGTA TAGA                                                       2 4
```

( 2 ) INFORMATION FOR SEQ ID NO:20:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
ACTGTAGACC GCGATCGCGA ACGCGAGC                                                   2 8
```

( 2 ) INFORMATION FOR SEQ ID NO:21:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
CTCGCGTTCG CGATCGCGGT CTACAGTAAG AGAG                                            3 4
```

( 2 ) INFORMATION FOR SEQ ID NO:22:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:22:

TTATCTCATG CATTTCCTCC                                                           20

( 2 ) INFORMATION FOR SEQ ID NO:23:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:23:

GTGTCGTGCT TCTAGACCA                                                            19

( 2 ) INFORMATION FOR SEQ ID NO:24:

( i ) SEQUENCE CHARACTERISTICS:
            ( A ) LENGTH: 31 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:24:

GCTATACACC GCGATCGCAA AAGCTACCAG C                                              31

( 2 ) INFORMATION FOR SEQ ID NO:25:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:25:

GGTAGCTTTT GCGATCGCGG TGTATAGCAG GA                                             32

( 2 ) INFORMATION FOR SEQ ID NO:26:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:26:

TACGGGCGCG CTCCATTAG                                                            19

( 2 ) INFORMATION FOR SEQ ID NO:27:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:27:

CCGATAGTTT GAGTTCTTCT ACTCAGGC                                                                28

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GAAGAAAGCG AAAGGAGCGG GCGCTAGGGC                                                              30

( 2 ) INFORMATION FOR SEQ ID NO:29:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GCACCCCGCT TGGGCAGAG                                                                          19

( 2 ) INFORMATION FOR SEQ ID NO:30:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GCACCCCGCT TGGGCAGAA                                                                          19

( 2 ) INFORMATION FOR SEQ ID NO:31:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GCACCCCGCT TGGGCAGAT                                                                          19

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

GCACCCCGCT TGGGCAGAC                                                                                              19

( 2 ) INFORMATION FOR SEQ ID NO:33:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:33:

TCCCGCCCCT CCTGGAAGAC                                                                                             20

( 2 ) INFORMATION FOR SEQ ID NO:34:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:34:

GATAAAGATA GACAAGGTAT AC                                                                                          22

( 2 ) INFORMATION FOR SEQ ID NO:35:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:35:

CGTATTCCTC GATTCTCTTT                                                                                             20

1

PURIFIED THERMOSTABLE NUCLEIC ACID POLYMERASE AND DNA CODING SEQUENCES FROM PYRODICTIUM SPECIES

FIELD OF THE INVENTION

The present invention relates to thermostable DNA polymerases from hyperthermophilic archael Pyrodictium species and means for isolating and producing the enzymes. Thermostable DNA polymerases are useful in many recombinant DNA techniques, especially nucleic acid amplification by the polymerase chain reaction (PCR).

BACKGROUND ART

Extensive research has been conducted on the isolation of DNA polymerases from mesophilic microorganisms such as *E. coli*. See, for example, Bessman et al., 1957, *J. Biol. Chem.* 223:171–177, and Buttin and Kornberg, 1966, *J. Biol. Chem.* 241:5419–5427.

Interest in DNA polymerases from thermophilic microbes increased with the invention of nucleic acid amplification processes. The use of thermostable enzymes, such as those described in U.S. Pat. No. 4,165,188, to amplify existing nucleic acid sequences in amounts that are large compared to the amount initially present was described U.S. Pat. Nos. 4,683,195 and 4,683,202, which describe the PCR process. These patents are incorporated herein by reference. The PCR process involves denaturation of a target nucleic acid, hybridization of primers, and synthesis of complementary strands catalyzed by a DNA polymerase. The extension product of each primer becomes a template for the production of the desired nucleic acid sequence. These patents disclose that, if the polymerase employed is a thermostable enzyme, then polymerase need not be added after every denaturation step, because heat will not destroy the polymerase activity.

The thermostable DNA polymerase from *Thermus aquaticus* (Taq) has been cloned, expressed, and purified from recombinant cells as described in Lawyer et al., 1989, *J. Biol. Chem.* 264:6427–6437, and U.S. Pat. Nos. 4,889,818 and 5,079,352, which are incorporated herein by reference. Crude preparations of a DNA polymerase activity isolated from *T. aquaticus* have been described by others (Chien et al., 1976, *J. Bacteriol.* 127:1550–1557, and Kaledin et al., 1980, Biokymiya 45:644–651).

U.S. Pat. No. 4,889,818, European Patent Publication No. 258,017, and PCT Publication No. 89/06691, the disclosures of which are incorporated herein by reference, all describe the isolation and recombinant expression of an ~94 kDa thermostable DNA polymerase from *Thermos aquaticus* and the use of that polymerase in PCR. Although *T. aquaticus* DNA polymerase is especially preferred for use in PCR and other recombinant DNA techniques, a number of other thermophilic DNA polymerases have been purified, cloned, and expressed. (See co-pending, commonly assigned PCT Patent Publication Nos. WO 91/09950, WO 92/03556, WO 92/06200, and WO 92/06202, which are incorporated heroin by reference.)

Thermostable DNA polymerases are not irreversibly inactivated even when heated to 93°–95° C. for brief periods of time, as, for example, in the practice of DNA amplification by PCR. In contrast, at this elevated temperature *E. coli* DNA Pol I is inactivated.

Archaeal hyperthermophiles, such as Pyrodictium and Methanopyrus species, grow at temperatures up to about 110° C. and are unable to grow below 80° C. (see, Stetter et al., 1990, *FEMS Microbiology Reviews* 75:1170124, which is incorporated herein by reference). These sulfur reducing, strict anaerobes are isolated from submarine environments. For example, *P. abyssi* was isolated from a deep sea active "smoker" chimney off Guaymas Mexico at 2,000 meters depth and in 320° C. of venting water (Pley et al., 1991, *Systematic and Applied Microbiology* 14:245). In contrast to the Pyrodictium species, other thermophilic microorganisms having an optimum growth temperature at or about 90° C. and a maximum growth temperature at or about 100° C. are not difficult to culture. For example, a gene encoding DNA polymerase has been cloned and sequenced from *Thermococcus litoralis* (EP No. 455,430).

In contrast, culture of the extreme hyperthermophilic microorganisms is made difficult by their inability to grow on agar solidified media. Individual cells of the Pyrodictium species are extremely fragile, and the organisms grow as fibrous networks. Standard bacterial fermentation techniques are extremely difficult for culturing Pyrodictium species due to the fragility of the cells and tendency of the cells to grow as networks clogging the steel parts of conventional fermentation apparatus. (See Staley, J. T. et al. eds., *Bergey's Manual of Systematic Bacteriology*, 1989, Williams and Wilkins, Baltimore, which is incorporated herein by reference.) These difficulties preclude laboratory culture for preparing large amounts of purified nucleic acid polymerase enzymes for characterization and amino acid sequence analysis. Those skilled in the art may be able to culture Pyrodictium to a cell density approaching $10^6$–$10^7$ cells/ml (see, for example, Phipps et al., 1991, *EMBO J.* 10(7):1711–1722). In contrast, *E. coli* is routinely grown to $0.3$–$1.0 \times 10^{11}$ cells/ml.

Accordingly, there is a need for the characterization, amino acid sequence, DNA sequence, and expression in a non-native host, of hyperthermophile DNA polymerase enzymes to eliminate the prior difficulties associated with the native host. In addition there is a desire in the art to produce thermostable DNA polymerases having enhanced thermostability that may be used to improve the PCR process and to improve the results obtained when using a thermostable DNA polymerase in other recombinant techniques such as DNA sequencing, nick-translation, and reverse transcription.

The present invention meets these needs by providing DNA and amino acid sequence information, recombinant expression vectors and purification protocols for DNA polymerases from Pyrodictium species.

SUMMARY OF THE INVENTION

The present invention provides thermostable enzymes that catalyze the combination of nucleoside triphosphates to form a nucleic acid strand complementary to a nucleic acid template strand. The enzymes are DNA polymerases from Pyrodictium species. In a preferred embodiment, the enzyme is from *P. occultum* or *P. abyssi*. This material may be used in a temperature-cycling amplification reaction wherein nucleic acid sequences are produced from a given nucleic acid sequence in amounts that are large compared to the amount initially present so that the sequences can be manipulated and/or analyzed easily.

The genes encoding the *P. occultum* and *P. abyssi* DNA polymerase enzyme have also been identified and cloned and provide yet another means to prepare the thermostable enzyme of the present invention. In addition, DNA and amino acid sequences of the genes encoding the *P. occultum* and *P. abyssi* enzyme and derivatives of these genes encoding *P. occultum* and *P. abyssi* DNA polymerase activity are also provided. In addition, modified genes encoding and expressing 3'-5' exonucleasedeficient forms of *Pyrodictium occultum* and *P. abyssi* DNA polymerase activity are also provided.

The invention also encompasses stable enzyme compositions comprising a purified, thermostable *P. occultum* and/or *P. abyssi* enzyme as described above in a buffer containing one or more non-ionic polymeric detergents.

Finally, the invention provides a method of purification for the thermostable polymerase of the invention.

DETAILED DESCRIPTION OF THE INVENTION

The present invention provides DNA sequences and expression vectors that encode Pyrodictium DNA polymerase. To facilitate understanding of the invention, a number of terms are defined below.

The terms "cell," "cell line," and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length gene sequence or by any portion of the coding sequence so long as the enzymatic activity is retained.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "mixture" as it relates to mixtures containing Pyrodictium polymerase refers to a collection of materials which includes Pyrodictium polymerase but which can also include other proteins. If the Pyrodictium polymerase is derived from recombinant host cells, the other proteins will ordinarily be those associated with the host. Where the host is bacterial, the contaminating proteins will, of course, be bacterial proteins.

The term "non-ionic polymeric detergents" refers to surface-active agents that have no ionic charge and that are characterized for purposes of this invention, by an ability to stabilize the Pyrodictium enzyme at a pH range of from about 3.5 to about 9.5, preferably from 4 to 9.0.

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage etak, 1981, *Tetrahedron Lett.* 22:1859–1862; the triester method of Matteucci et al., 1981, *J. Am. Chem. Soc.* 103:3185–3191 or automated synthesis methods; and the solid support method of U.S. Pat. No. 4,458,066.

The term "primer" as used herein refers to an oligonucleotide, whether natural or synthetic, which is capable of acting as a point of initiation of synthesis when placed under conditions in which primer extension is initiated. Synthesis of a primer extension product which is complementary to a nucleic acid strand is initiated in the presence of nucleoside triphosphates and a DNA polymerase or reverse transcriptase enzyme in an appropriate buffer at a suitable temperature. A "buffer" includes cofactors (such as divalent metal ions) and salt (to provide the appropriate ionic strength), adjusted to the desired pH. For Pyrodictium polymerases, the buffer preferably contains 1 to 3 mM of a magnesium salt, preferably $MgCl_2$, 50 to 200 µM of each nucleotide, and 0.2 to 1 µM of each primer, along with 10–100 mM KCl, 10 mM Tris buffer (pH 7.5–8.5), and 100 µg/ml gelatin (although gelatin is not required, and should be avoided in some applications, such as DNA sequencing).

A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template.

The term "primer" may refer to more than one primer, particularly in the case where there is some ambiguity in the information regarding one or both ends of the target region to be amplified. For instance, if a nucleic acid sequence is inferred from a protein sequence, a "primer" is actually a collection of primer oligonucleotides containing sequences representing all possible codon variations based on the degeneracy of the genetic code. One of the primers in this collection will be homologous with the end of the target sequence. Likewise, if a "conserved" region shows significant levels of polymorphism in a population, mixtures of primers can be prepared that will amplify adjacent sequences.

A primer may be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISAS), biotin, or haptens and proteins for which antisera or monoclonal antibodies are available. A label can also be used to "capture" the primer, so as to facilitate the immobilization of either the primer or a primer extension product, such as amplified DNA, on a solid support.

The terms "restriction endonucleases" and "restriction enzymes" refer to bacterial enzymes which cut double-stranded DNA at or near a specific nucleotide sequence.

The terms "thermostable polymerase" and "thermostable enzyme" refer to an enzyme which is stable to heat and is heat resistant and catalyzes combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates.

The Pyrodictium thermostable enzymes of the present invention satisfy the requirements for effective use in the amplification reaction known as the polymerase chain reaction or PCR as described in U.S. Pat. No. 4,965, 188 (incorporated herein by reference). The Pyrodictium enzymes do not become irreversibly denatured (inactivated) when subjected to the elevated temperatures for the time necessary to effect denaturation of double-stranded nucleic acids, a key step in the PCR process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° C. to about 105° C. for a time depending mainly on the temperature and the nucleic acid length, typically from a few seconds up to four minutes.

Higher temperatures may be required as the buffer salt concentration and/or GC composition of the nucleic acid is increased. The Pyrodictium enzymes do not become irreversibly denatured from relatively short exposures to temperatures of about 95° C.–100° C. The extreme thermostability of the Pyrodictium DNA polymerase enzymes provides additional advantages over previously characterized thermostable enzymes. Prior to the present invention, efficient PCR at denaturation temperatures as high as 100° C. had not been demonstrated. No thermostable DNA polymerases have been described for this purpose. However, as the G/C content of a target nucleic acid increases, the temperature necessary to denature ($T_{den}$), the duplex also increases. For target sequences that require a $T_{den}$ step of over 95° C., previous protocols require that solvents are included in the PCR for partially destabilizing the duplex, thus, lowering the effective $T_{den}$. Agents such as glycerol, DMSO, or formamide have been used in this manner in PCR (Korge et al., 1992, *Proc. Natl. Acad. Sci. U.S.A.* 89:910–914, and Wong et al., 1991, *Nuc. Acids Res.* 19:225 1–2259, incorporated herein by reference). These agents, in addition to destabilizing duplex DNA will affect primer stability, can inhibit enzyme activity, and varying concentrations of DMSO or formamide decrease the thermoresistance (i.e., half-life) of thermophilic DNA polymerases. Accordingly, a significant number of optimization experiments and reaction conditions need to be evaluated when utilizing these cosolvents. In contrast, simply raising the $T_{den}$ to 100° C. with Pot or Pab DNA polymerase in an otherwise standard PCR can facilitate complete strand separation of PCR product eliminating the need for DNA helix destabilizing agents.

The extreme hyperthermophilic polymerases disclosed herein are stable at temperatures exceeding 100° C., and even as high as 110° C. However, at these temperatures depending on the pH and ionic strength, the integrity of the target DNA may be adversely affected (Ekert and Kunkel, 1992, *In PCR: A Practical Approach*, eds. McPherson, Quirke and Taylor, Oxford University Press, pages 225–244, incorporated herein by reference).

The Pyrodictium DNA polymerase has an optimum temperature at which it functions that is higher than about 45° C. Temperatures below 45° C. facilitate hybridization of primer to template, but depending on salt composition and concentration and primer composition and length, hybridization of primer to template can occur at higher temperatures (e.g., 45°–70° C.), which may promote specificity of the primer hybridization reaction. The enzymes of the invention exhibit activity over a broad temperature range up to 85° C. The optimal activity is template dependent and generally in the range of 70°–80° C.

The present invention provides DNA sequences encoding the thermostable DNA polymerase activity of Pyrodictium species. The preferred embodiments of the invention provide the nucleic acid and amino acid sequences for *P. abyssi* and *P. occultum* DNA polymerase. The entire *P. abyssi* and *P. occultum* DNA polymerase coding sequences are depicted below as SEQ ID No. 1 (*P. abyssi*) and SEQ ID No. 3 (*P. occultum*). The deduced amino acid sequences are listed as SEQ ID No. 2 (*P. abyssi*) and SEQ ID No. 4 (*P. occultum*). For convenience, the nucleotide and amino acid sequences of these polymerases are numbered for reference.

The present invention provides nucleic acid sequences providing means for comparison of *P. occultum* and *P. abyssi* DNA polymerase sequences with other thermostable polymerase enzymes. Such a comparison demonstrates that these novel sequences are unrelated to previously described nucleic acid sequences encoding eubacterial thennostable DNA polymerases. Consequently, methods for identifying Pyrodictium DNA polymerase enzymes based on the published sequences of known eubacterial thermostable DNA polymerases are not suitable for isolating nucleic acid sequences encoding Pyrodictium DNA polymerase enzymes.

P. abyssi DNA Polymerase
SEQ ID No. 1                                        ATGCCAGAAGCTATAGAGTTCGTGCTCCTT
SEQ ID No. 2                                        Met Pro Glu Ala Ile  Glu Phe Val Leu Leu    10

31 GATTCAAGCTACGAGATTGTAGGGAAAGAGCCGGTAATCATACTATGGGGTGTAACGCTA
     Asp Ser Ser Tyr Glu Ile  Val Gly Lys Glu Pro Val Ile  Ile  Leu Trp Gly Val Thr Leu    30

91 GACGGTAAACGCATAGTCCTACTTGATAGGAGGTTTAGGCCCTACTTCTATGCACTCATA
     Asp Gly Lys Arg Ile  Val Leu Leu Asp Arg Arg Phe Arg Pro Tyr Phe Tyr Ala Leu Ile      50

151 TCCCGCGACTACGAAGGTAAGGCCGAGGAGGTAGTAGCTGCTATTAGAAGGCTAAGTATG
     Ser Arg Asp Tyr Glu Gly Lys Ala Glu Glu Val Val Ala Ala Ile  Arg Arg Leu Ser Met     70

211 GCAAAGAGCCCCATAATAGAAGCAAAGGTGGTTAGTAAGAAGTACTTCGGAAGGCCCCGT
     Ala Lys Ser Pro Ile  Ile  Glu Ala Lys Val Val Ser Lys Lys Tyr Phe Gly Arg Pro Arg    90

271 AAAGCAGTCAAAGTAACGACAGTTATACCCGAATCTGTCAGAGAATATAGAGAGGCTGTA
     Lys Ala Val Lys Val Thr Thr Val Ile  Pro Glu Ser Val Arg Glu Tyr Arg Glu Ala Val    110

331 AAAAAGCTGGAAGGCGTGGAAGACTCTCTAGAAGCAGACATAAGGTTCGCGATGAGGTAT
     Lys Lys Leu Glu Gly Val Glu Asp Ser Leu Glu Ala Asp Ile  Arg Phe Ala Met Arg Tyr    130

391 CTAATCGACAAGAAGCTCTACCCGTTCACAGCATACCGTGTCAGAGCCGAGAACGCTGGA
     Leu Ile  Asp Lys Lys Leu Tyr Pro Phe Thr Ala Tyr Arg Val Arg Ala Glu Asn Ala Gly    150

451 CGCAGCCCTGGTTTCCGTGTAGACTCGGTATACACTATAGTTGAGGACCCAGAGCCTATT
     Arg Ser Pro Gly Phe Arg Val Asp Ser Val Tyr Thr Ile  Val Glu Asp Pro Glu Pro Ile    170

511 GCCGACATAACTAGTATAGATATACCAGAGATGCGTGTGCTCGCGTTCGACATAGAGGTC
     Ala Asp Ile  Thr Ser Ile  Asp Ile  Pro Glu Met Arg Val Leu Ala Phe Asp Ile  Glu Val   190

571 TACAGTAAGAGAGGAAGCCCTAACCCGTCCCGCGACCCGGTCATAATAATCTCGATAAAG
     Tyr Ser Lys Arg Gly Ser Pro Asn Pro Ser Arg Asp Pro Val Ile  Ile  Ile  Ser Ile  Lys   210

631 GACAGCAAGGGGAACGAGAAGCTACTAGAAGCCAATAACTACGACGACAGAAACGTGCTA
     Asp Ser Lys Gly Asn Glu Lys Leu Leu Glu Ala Asn Asn Tyr Asp Asp Arg Asn Val Leu    230

691 CGGGAATTTATAGAGTACATACGCTCCTTTGACCCAGACATAATAGTAGGCTACAATAGC
     Arg Glu Phe Ile  Glu Tyr Ile  Arg Ser Phe Asp Pro Asp Ile  Ile  Val Gly Tyr Asn Ser   250

751 AACAATTTTGACTGGCCATACCTTATAGAACGTGCACACAGAATAGGAGTAAAGCTCGAC
     Asn Asn Phe Asp Trp Pro Tyr Leu Ile  Glu Arg AlA His Arg Ile  Gly Val Lys Leu Asp    270

811 GTGACAAGGCGTGTTGGCGCAGAGCCAAGTATGAGCGTCTATGGACATGTCTCAGTGCAG
     Val Thr Arg Arg Val Gly Ala Glu Pro Ser Met Ser Val Tyr Gly His Val Ser Val Gln    290

871 GGTAGGCTAAACGTAGACCTCTACAACTACGTGGAGGAAATGCATGAGATAAAGGTAAAG
     Gly Arg Leu Asn Val Asp Leu Tyr Asn Tyr Val Glu Glu Met His Glu Ile  Lys Val Lys    310

931 ACGCTCGAGGAGGTCGCCGAATACCTAGGCGTTATGCGCAAGAGCGAGCGCGTACTAATA
     Thr Leu Glu Glu Val Ala Glu Tyr Leu Gly Val Met Arg Lys Ser Glu Arg Val Leu Ile    330

991 GAATGGTGGCGGATCCCAGATTACTGGGACGACGAGAAGAAACGGCCGCTACTGAAGCGT
     Glu Trp Trp Arg Ile  Pro Asp Tyr Trp Asp Asp Glu Lys Lys Arg Pro Leu Leu Lys Arg    350

1051 TATGCCCTCGACGATGTGAGAGCCACCTACGGCCTCGCCGAGAAGATACTCCCATTCGCA
     Tyr Ala Leu Asp Asp Val Arg Ala Thr Tyr Gly Leu Ala Glu Lys Ile  Leu Pro Phe Ala    370

1111 ATACAGCTTTCGACAGTAACCGGTGTTCCTTTAGACCAAGTCGGGGCTATGGGCGTAGGT
     Ile  Gln Leu Ser Thr Val Thr Gly Val Pro Leu Asp Gln Val Gly Ala Met Gly Val Gly    390

1171 TTCCGTCTAGAATGGTACCTTATGAGAGCAGCGCATGATATGAACGAGCTTGTCCCCAAC
     Phe Arg Leu Glu Trp Tyr Leu Met Arg Ala Ala His Asp Met Asn Glu Leu Val Pro Asn    410

1231 CGTGTCAAGCGGCGCGAAGAGAGCTACAAGGGAGCAGTAGTACTAAAGCCCCTAAAGGGT
     Arg Val Lys Arg Arg Glu Glu Ser Tyr Lys Gly Ala Val Val Leu Lys Pro Leu Lys Gly    430

1291 GTCCATGAGAACGTAGTAGTGCTCGACTTTAGCTCAATGTACCCCAACATAATGATAAAG
     Val His Glu Asn Val Val Val Leu Asp Phe Ser Ser Met Tyr Pro Asn Ile  Met Ile  Lys   450

1351 TACAATGTGGGCCCTGACACGATAATTGACGACCCCTCAGAGTGCGAGAAGTACAGTGGA
     Tyr Asn Val Gly Pro Asp Thr Ile  Ile   Asp Asp Pro Ser GTluCys Glu Lys Tyr Ser Gly   470

1411 TGCTACGTAGCCCCCGAAGTCGGGCACATGTTTAGGCGCTCGCCCTCCGGCTTCTTTAAG
     Cys Tyr Val Ala Pro Glu Val Gly His Met Phe Arg Arg Ser Pro Ser Gly Phe Phe Lys    490

1471 ACCGTGCTTGAGAACCTCATAGCGCTGCGTAAGCAAGTACGTGAAAAGATGAAGGAGTTC
     Thr Val Leu Glu Asn Leu Ile  Ala Leu Arg Lys Gln Val Arg Glu Lys Met Lys Glu Phe    510

1531 CCCCCAGATAGCCCAGAATACCGGATATACGATGAACGCCAGAAGGCACTCAAGGTGCTA
     Pro Pro Asp Ser Pro Glu Tyr Arg Ile  Tyr Asp Glu Arg Gln lys Ala Leu Lys Val Leu    530

1591 GCCAACGCTAGCTACGGCTACATGGGATGGGTGCACGCTCGCTGGTACTGTAAACGCTGC
     Ala Asn Ala Ser Tyr Gly Tyr Met Gly Trp Val His Ala Arg Trp Tyr Cys Lys Arg Cys    550

-continued

```
1651 GC AGAGGCT GT AAC AGCCT GGGGCC GT AACCT GAT ACT CT C AGC AAT AGAAT AT GCT AGG
     Ala Glu Ala Val Thr Ala Trp Gly Arg Asn Leu Ile  Leu Ser Ala Ile  Glu Tyr Ala Arg  570

1711 AAGCT CGGCCT C AAAGT AAT AT AC GGAGAC AC GGACT CCCT ATT CGT AACCT ATG AT ATC
     Lys Leu Gly Leu Lys Val Ile  Tyr Gly Asp Thr Asp Ser Leu Phe Val Thr Tyr Asp Ile  590

1771 GAGAAGGT AAAGAAGCT AAT AGAATT CGT CGAGAAAC AGCT AGGCTT CGAGAT AAAGAT A
     Glu Lys Val Lys Lys Leu Ile  Glu Phe Val Glu Lys Gln Leu Gly Phe Glu Ile  Lys Ile  610

1831 GAC AAGGT AT AC AAAAGAGT GTT CTTT ACC GAGGC AAAGAAGCGCT ACGT GGGCCT CCT C
     Asp Lys Val Tyr Lys Arg Val Phe Phe Thr Glu Ala Lys Lys Arg Tyr Val Gly Leu Leu  630

1891 GAGGAC GGGC GT AT GGAC AT AGT AGGCT TT GAGGCT GTT AGAGGC GACT GGT GT GAGCT A
     Glu Asp Gly Arg Met Asp Ile  Val Gly Phe Glu Ala Val Arg Gly Asp Trp Cys Glu Leu  650

1951 GCT AAAGAGGT GC AAGAGAAAGT AGC AGAGAT AAT ACT GAAGAC GGGAGAC AT AAAT AGA
     Ala Lys Glu Val Gln Glu Lys Val Ala Glu Ile  Ile  Leu Lys Thr Gly Asp Ile  Asn Arg  670

2011 GCC AT AAGCT AC AT AAGAGAGGT CGT GAGAAAGCT AAGAGAAGGC AAGAT ACCC AT AAC A
     Ala Ile  Ser Tyr Ile  Arg Glu Val Val Arg Lys Leu Arg Glu Gly Lys Ile  Pro Ile  Thr  690

2071 AAGCT CGT AAT AT GGAAGACCTT GAC AAAGAGAAT CGAGGAAT ACGAGC ACGAGGC GCC G
     Lys Leu Val Ile  Trp Lys Thr Leu Thr Lys Arg Ile  Glu Glu Tyr Glu His Glu Ala Pro  710

2131 C ACGTT ACT GC AGC ACGGC GT AT GAAAGAAGC AGGCT ACGAT GT GGC ACC GGGAGAC AAG
     His Val Thr Ala Ala Arg Arg Met Lys Glu Ala Gly Tyr Asp Val Ala Pro Gly Asp Lys  730

2191 AT AGGCT AC AT C AT AGTT AAAGGAC AT GGC AGT AT ATC GAGT CGT GCCT ACCC GT ACTTT
     Ile  Gly Tyr Ile  Ile  Val Lys Gly His Gly Ser Ile  Ser Ser Arg Ala Tyr Pro Tyr Phe  750

2251 AT GGT AGACT CGT CT AAGGTT GAC AC AGAGT ACT AC AT AGACC ACC AGAT AGT ACC AGC A
     Met Val Asp Ser Ser Lys Val Asp Thr Glu Tyr Tyr Ile  Asp His Gln Ile  Val Pro Ala  770

2311 GC AAT GAGGAT ACT CT C AT ACTT CGGGGT C AC AGAGAAGC AGCTT AAGGC AGC AT C AT CT
     Ala Met Arg Ile  Leu Ser Tyr Phe Gly Val Thr Glu Lys Gln Leu Lys Ala Ala Ser Ser  790

2371 GGGC AT AGGAGT CT CTT CGACTT CT TY CGCGGC AAAGAAGT AGccccggctctccaaacta
     Gly His Arg Ser Leu Phe Asp Phe Phe  Ala Ala Lys Lys  *                           803
```

P. occultum DNA Polymerase

```
SEQ ID No. 3                        AT GAC AGAGACT AT AGAGTT CGT GCT GCT A
SEQ ID No. 4                        Met Thr Glu Thr Ile  Glu Phe Val Leu Leu    10

31 GACT CT AGCT ACGAGAT ACT GGGGAAGGAGCC GGT AGT AAT CCT CT GGGGGAT AAC GCTT
     Asp Ser Ser Tyr Glu Ile  Leu Gly Lys Glu Pro Val Val Ile  Leu Trp Gly Ile  Thr Leu  30

91 GACGGT AAACGT GT CGT GCTT CT AGACC ACC GCTT CCGCCCCT ACTT CT ACGCCCT C AT A
     Asp Gly Lys Arg Val Val Leu Leu Asp His Arg Phe Arg Pro Tyr Phe Tyr Ala Leu Ile   50

151 GCCC GGGGCT AT GAGGAT AT GGT GGAGGAGAT AGC AGCTT CC AT AAGGAGGCTT AGT GT G
     Ala Arg Gly Tyr Glu Asp Met Val Glu Glu Ile  Ala Ala Ser Ile  Arg Arg Leu Ser VaL  70

211 GT C AAGAGT CC GAT AAT AGAT GCC AAGCCT CTT GAT AAGAGGT ACTT CGGC AGGCCCC GT
     Val Lys Ser Pro Ile  Ile  Asp Ala Lys Pro Leu Asp Lys Arg Tyr Phe Gly Arg Pro Arg  90

271 AAGGCGGT GAAGATT ACC ACT AT GAT ACCC GAGT CT GTT AGAC ACT ACC GC GAGGC GGT G
     Lys Ala Val Lys Ile  Thr Thr Met Ile  Pro Glu Ser Val Arg His Tyr Arg Glu Ala Val  110

331 AAGAAGAT AGAGGGT GT GGAGGACT CCCT CGAGGC AGAT AT AAGGTTT GC AAT GAGAT AT
     Lys Lys Ile  Glu Gly Val Glu Asp Ser Leu Glu Ala Asp Ile  Arg Phe Ala Met Arg Tyr  130

391 CT GAT AGAT AAGAGGCT CT ACCC GTT C ACGGTTT ACC GGAT CCCC GT AGAGGAT GC GGGC
     Leu Ile  Asp Lys Arg Leu Tyr Pro Phe Thr Val Tyr Arg Ile  Pro Val Glu Asp Ala Gly  150

451 C GC AAT CC AGGCTT CC GT GTT GAC CGT GT CT AC AAGGTT GCT GGC GACCC GGAGCCCCT A
     Arg Asn Pro Gly Phe Arg Val Asp Arg Val Tyr Lys Val Ala Gly Asp Pro Glu Pro Leu  170

511 GC GGAT AT AAC GC GGAT CGACCTT CCCCC GAT GAGGCT GGT AGCTTTT GAT AT AGAGGT G
     Ala Asp Ile  Thr Arg Ile  Asp Leu Pro Pro Met Arg Leu Val Ala Phe Asp Ile  Glu Val  190

571 T AT AGC AGGAGGGGGAGCCCT AACCCT GC AAGGGAT CC AGT GAT AAT AGT GT CGCT GAGG
     Tyr Ser Arg Arg Gly Ser Pro Asn Pro Ala Arg Asp Pro Val Ile  Ile  Val Ser Leu Arg  210

631 GAC AGC GAGGGC AAGGAGAGGCT C AT AGAAGCT GAAGGCC AT GACGAC AGGAGGGTT CT G
     Asp Ser Glu Gly Lys Glu Arg Leu Ile  Glu Ala Glu Gly His Asp Asp Arg Arg Val Leu  230

691 AGGGAGTT CGT AGAGT ACGT GAGAGCCTT CGACCCC GAC AT AAT AGT GGGCT AT AAC AGT
     Arg Glu Phe Val Glu Tyr Val Arg Ala Phe Asp Pro Asp Ile  Ile  Val Gly Tyr Asn Ser  250

751 AACC ACTT CGACT GGCCCT ACCT AAT GGAGCGCGCCC GT AGGCT CGGGATT AACCT CGAC
     Asn His Phe Asp Trp Pro Tyr Leu Met Glu Arg Ala Arg Arg Leu Gly Ile  Asn Leu Asp  270

811 GTT AC ACGCC GT GT GGGGGC AGAGCCC ACC ACC AGC GT CT ACGGCC ACGT CT CGGT GC AG
     Val Thr Arg Arg Val Gly Ala Glu Pro Thr Thr Ser Val Tyr Gly His Val Ser Val Gln  290
```

-continued

```
 871 GGT AGGCT GAA CGT GGA CCT CT ACG ACT AT GCC GAG GAG AT GCC GGA GAT AAA GAT GAA G
     Gly Arg Leu Asn Val Asp Leu Tyr Asp Tyr Ala Glu Glu Met Pro Glu Ile  Lys Met Lys  310

931 ACG CTT GAG GAG GT AGC GGA GT ACCT AGG CGT T AT GAA GAA GAG CGA GCG T GT GAT AAT A
     Thr Leu Glu Glu Val Ala Glu Tyr Leu Gly Val Met Lys Lys Ser Glu Arg Val Ile  Ile   330

991 GAG T GGT GGA GGA T ACC CGA GT ACT GGG AT GAC GAG AAG AAG AGG CAG CT GCT AGA GCG C
     Glu Trp Trp Arg Ile  Pro Glu Tyr Trp Asp Asp Glu Lys Lys Arg Gln Leu Leu Glu Arg  350

1051 T ACG CGC T CGA CGA T GT GAG GGC T ACC T ACG GCC T CGC GGA AAA GAT GCT ACC GTT CGC C
     Tyr Ala Leu Asp Asp Val Arg Ala Thr Tyr Gly Leu Ala Glu Lys Met Leu Pro Phe Ala  370

1111 AT ACA GCT CT CCA CT GTT ACG GGT GT GCC TCT CGA CCA GGT AGG T GCT AT GGG CGT AGG C
     Ile  Gln Leu Ser Thr Val Thr Gly Val Pro Leu Asp Gln Val Gly Ala Met Gly Val Gly  390

1171 TT CCG CCT AGA GT GGT AT CT CAT GCG T GCA GCC T ACG AT AT GAA CGA GCT GGT GCC GAA C
     Phe Arg Leu Glu Trp Tyr Leu Met Arg Ala Ala Tyr Asp Met Asn Glu Leu Val Pro Asn  410

1231 C GGG T GGA GAG GAG GGG GGG A GAG CT ACA AGG GT GCA GT AGT GTT AAA GCC TCT CAA GGA
     Arg Val Glu Arg Arg Gly Glu Ser Tyr Lys Gly Ala Val Val Leu Lys Pro Leu Lys Gly  430

1291 GT CCA T GAG AAT GTT GT GGT GCT CGA TTT CAG TT CCA T GT ACC CGA GCA TAA T GAT AAA G
     Val His GLu Asn Val Val Val Leu Asp Phe Ser Ser Met Tyr Pro ser Ile  Met Ile  Lys  450

1351 T ACA ACG TGG GCC CCG ACA CTA T AGT CGA CGA CCC CT CGG AGT GCC CAA AGT ACG GCG GC
     Tyr Asn Val Gly Pro Asp Thr Ile  Val Asp Asp Pro Ser Glu Cys Pro Lys Tyr Gly Gly  470

1411 T GCT AT GT AGC CCC CGA GGT CGG GCA CCG GTT CCG TCG CTC CCC GCC AGG CTT CTT CAA G
     Cys Tyr Val Ala Pro Glu Val Gly His Arg Phe Arg Arg Ser Pro Pro Gly Phe Phe Lys  490

1471 ACC GT GCT CGA GAA CCT ACT GAA GCT ACG CCG ACA GGT AAA GGA GAA GAT GAA GGA GTT T
     Thr Val Leu Glu Asn Leu Leu Lys Leu Arg Arg Gln Val Lys Glu Lys Met Lys Glu Phe  510

1531 CCG CCT GAC AGC CCC GAG TAC AGG CT CT ACG AT GAG CGC CAG AAG GCG CTC AAG GTT CTT
     Pro Pro Asp Ser Pro Glu Tyr Arg Leu Tyr Asp Glu Arg Gln Lys Ala Leu Lys Val Leu  530

1591 GCG AAC GCG AGC T AT GGC T ACA T GGG GT GGA GCC AT GCC CGC TGG T ACT GCA AAC GCT GC
     Ala Asn Ala Ser Tyr Gly Tyr Met Gly Trp Ser His Ala Arg Trp Tyr Cys Lys Arg Cys  550

1651 GCC GAG GCT GT CAC AGC CTG GGG CCG T AAC CTT AT ACT GAC AGC T AT CGA GT AT GCC AGG
     Ala Glu Ala Val Thr Ala Trp Gly Arg Asn Leu Ile  Leu Thr Ala Ile  Glu Tyr Ala Arg  570

1711 AAG CTC GGC CTA AAG GTT AT AT AT GGA GAC ACC GAC TCC CT CTT CGT GGT CT AT GAC AAG
     Lys Leu Gly Leu Lys Val Ile  Tyr Gly Asp Thr Asp Ser Leu Phe Val Val Tyr Asp Lys  590

1771 GAG AAG GTT GAG AAG CTG AT AGA GTT T GT CGA GAA GGA GCT GGG CTT T GAG AT AAA GAT A
     Glu Lys Val Glu Lys Leu Ile  Glu Phe Val Glu Lys Glu Leu Gly Phe Glu Ile  Lys Ile   610

1831 GAC AAG AT CT ACA AGA AAG T GTT CTT CAC GGA GGC TAA GAA GCG CT AT GT AGG TCT CCT C
     Asp Lys Ile  Tyr Lys Lys Val Phe Phe Thr Glu Ala Lys Lys Arg Tyr Val Gly Leu Leu  630

1891 GAG GAC GGA CGT AT AGA CAT CGT GGG CTT T GAA GCA GTC CGC GGC GAC T GGT GCG AGC TG
     Glu Asp Gly Arg Ile  Asp Ile  Val Gly Phe Glu Ala Val Arg Gly Asp Trp Cys Glu Leu  650

1951 GCT AAG GAG GT GCA GGA GAA GGC GGC T GAG AT AGT GTT GAA T ACG GGG AAC GT GGA CAA G
     Ala Lys Glu Val Gln Glu Lys Ala Ala Glu Ile  Val Leu Asn Thr Gly Asn Val Asp Lys  670

2011 GCT AT AAG CT ACA T AAG GGA GGT AAT AAA GCA GCT CCG CGA GGG CAA GGT GCC AAT AAC A
     Ala Ile  Ser Tyr Ile  Arg Glu Val Ile  Lys Gln Leu Arg Glu Gly Lys Val Pro Ile  Thr   690

2071 AAG CTT AT CAT AT GGA AGA CGC T GAG CAA GAG GAT AGA GGA GT ACG AGC AT GAC GCG CCT
     Lys Leu Ile  Ile  Trp Lys Thr Leu Ser Lys Arg Ile  Glu Glu Tyr Glu His Asp Ala Pro  710

2131 CAT GT GAT GGC T GCA CGG CGT AT GAA GGA GGC AGG CT ACG AGG T GT CTC CCG GCG AT AAG
     His Val Met Ala Ala Arg Arg Met Lys Glu Ala Gly Tyr Glu Val Ser Pro Gly Asp Lys  730

2191 GT GGG CT ACG T CAT AGT T AAG GGT AGC GGG AGT GT GT CCA GCA GGG CCT ACC CCT ACT TC
     Val Gly Tyr Val Ile  Val Lys Gly Ser Gly Ser Val Ser Ser Arg Ala Tyr Pro Tyr Phe  750

2251 AT GGT T GAT CCA TCG ACC AT CGA CGT CAA CTA CT AT ATT GAC CAC CAG AT AGT GCC GGC T
     Met Val Asp Pro Ser Thr Ile  Asp Val Asn Tyr Tyr Ile  Asp His Gln Ile  Val Pro Ala  770

2311 GCT CT GAG GAT ACT CTC CTA CTT CGG AGT CAC CGA GAA ACA GCT CAA GGC GGC GGC T ACG
     Ala Leu Arg Ile  Leu Ser Tyr Phe Gly Val Thr Glu Lys Gln Leu Lys Ala Ala Ala Thr  790

2371 GT GCA GAG AAG CCT CTT CGA CTT CTT CGC CCT CAA AGA AAT AGctcctccacccggctagc
     Val Gln Arg Ser Leu Phe Asp Phe Phe Ala Ser Lys Lys   *                            803
```

As a result of the present invention, Pyrodictium DNA polymerase amino acid sequences can be used to design novel degenerate primers to find new, previously undiscovered hyperthermic DNA polymerase genes. The generic utility of the degenerate primer process is exemplified in WO 92/06202, which is incorporated herein by reference. The publication describes the use of degenerate primers for cloning the gene encoding *Thermosipho africanus* DNA polymerase. Prior to the present invention, degenerate priming methods were demonstrated to be suitable for isolating genes encoding novel thermostable DNA polymerase enzymes. The success of these methods lies in part in the identification of conserved motifs among the thermostable DNA polymerases of, for example, *Thermus aquaticus* and *Thermus thermophilus*.

Thus, due to the dissimilarity in DNA polymerase amino acid sequences between the extreme hyperthermophiles, for example, Pyrodictium species, and nonhyperthermophiles such as Thermus species these degenerate priming methods were not previously suitable for isolating and expressing pyrodictium polymerase genes. Applicants' invention has enabled the use of degenerate priming methods for isolating genes encoding novel DNA polymerase enzymes from extreme hyperthermophilic microbes. The gene encoding the DNA polymerase of the hyperthermophilic *T. litoralis* (Tli) has been described. While Tli, Pab and Poc DNA polymerases contain the amino acid sequence motifs that reflect eucaryotic DNA polymerases, Pab and Poc DNA polymerases have only limited and spotty amino acid sequence identity with Tli DNA polymerase. Specifically, amino acid sequence alignments indicate only 37% to 39% sequence identity between Poc or Pab with Tli DNA polymerase. Significant regions of non-identity with Tli DNA polymerase occur in the 20 amino acids that precede and the 10 amino acids that follow Region 1 (position 438 through 458 in SEQ ID Nos. 2 and 4). In addition, significant regions on non-identity with Tli DNA polymerase occur in the 10 to 15 amino acids that precede, and the 10 to 15 amino acids that follow Region 4 (position 611 through 634 in SEQ ID Nos. 2 and 4). These regions as well as other portions of the polymerase active site are highly conserved in Poc and Pab DNA polymerases and contribute significantly to the extraordinary thermostability of these DNA polymerase enzymes.

The present invention, by providing DNA and amino acid sequences for two Pyrodictium polymerase enzymes, therefore, enables the isolation of other extremely thermophilic DNA polymerase enzymes and the coding sequences for those enzymes. Further alignment of *P. occultum* and *P. abyssi* sequences with known thermostable enzyme sequences allows the selective identification of additional novel enzymes suitable for efficient PCR at denaturation temperatures of 100° C.

The DNA and amino acid sequences shown above and the DNA compounds that encode those sequences can be used to design and construct recombinant DNA expression vectors to drive expression of Pyrodictium DNA polymerase activity in a wide variety of host cells. A DNA compound encoding all or part of the DNA sequence shown above can also be used as a probe to identify thermostable polymerase-encoding DNA from other archaea, especially Pyrodictium species and the amino acid sequence shown above can be used to design peptides for use as immunogens to prepare antibodies that can be used to identify and purify a thermostable polymerase.

Recombinant vectors that encode an amino acid sequence encoding a Pyrodictium DNA polymerase will typically be purified prior to use in a recombinant DNA technique. The present invention provides such purification methodology.

The molecular weight of the DNA polymerase purified from recombinant *E. coli* host which express the *P. occultum* or *P. abyssi* polymerase genes are determined by the above method to be about 90 kDa. The molecular weight of this same DNA polymerase as determined by the predicted amino acid sequence is calculated to be approximately 92.6 kilodaltons.

An important aspect of the present invention is the production of recombinant Pyrodictium DNA polymerase. As noted above, the gene encoding this enzyme has been cloned from two exemplary Pyrodictium species, *P. occultum* and *P. abyssi*, genomic DNA. The complete coding sequence for the *P. occultum* (Poc) DNA polymerase can be easily obtained in an ~2.52 kb NheI restriction fragment of plasmid pPoc 4. This plasmid was deposited with the American Type Culture Collection (ATCC) in host cell *E. coli* Sure® Cells (Stratagene) on May 11, 1993, under Accession No. 69309. The complete coding sequence for *P. abyssi* (Pab) DNA polymerase can be easily obtained in an ~3.74 kb SalI restriction fragment of plasmid pPab 14. This plasmid was deposited with the ATCC in host cell *E. coli* Sure® Cells (Stratagene) on May 11, 1993, and under Accession No. 69310.

The complete coding sequence and deduced amino acid sequence of the thermostable Pab and Poc DNA polymerase enzymes are provided above. The entire coding sequence of the DNA polymerase gene is not required, however, to produce a biologically active gene product with DNA polymerase activity. The availability of DNA encoding the Pyrodictium DNA polymerase sequence provides the opportunity to modify the coding sequence so as to generate mutein (mutant protein) forms also having DNA polymerase activity. Amino(N)-terminal deletions of approximately one-third of the coding sequence can provide a gene product that is quite active in polymerase assays. Because certain N-terminal shortened forms of the polymerase are active, the gene constructs used for expression of these polymerases can include the corresponding shortened forms of the coding sequence.

In addition to the N-terminal deletions, individual amino acid residues in the peptide chain comprising Pyroclictium polymerase may be modified by oxidation, reduction, or other derivation, and the protein may be cleaved to obtain fragments that retain activity. Such alterations that do not destroy activity do not remove the protein from the definition of a protein with Poc or Pab polymerase activity and so are specifically included within the scope of the present invention. Modifications to the primary structure of the Poc or Pab DNA polymerase gene by deletion, addition, or alteration so as to change the amino acids incorporated into the DNA polymerase during translation can be made without destroying the high temperature DNA polymerase activity of the protein. Such substitutions or other alternations result in the production of proteins having an amino acid sequence encoded by DNA falling within the contemplated scope of the present invention. Likewise, the cloned genomic sequence, or homologous synthetic sequences, of the Poc and Pab DNA polymerase genes can be used to express fusion polypeptides with Pyrodictium DNA polymerase activity or to express a protein with an amino acid sequence identical to that of native Poc or Pab DNA polymerase.

Thus, the present invention provides the complete coding sequence for Pab and Poc DNA polymerase enzymes from which expression vectors applicable to a variety of host systems can be constructed and the coding sequence expressed. Portions of the present polymerase-encoding sequence are also useful as probes to retrieve other thermostable polymerase-encoding sequences in a variety of species. Accordingly, portions of the genomic DNA encoding at least four to six amino acids can be synthesized as oligodeoxyribonucleotide probes that encode at least four to six amino acids and used to retrieve additional DNAs encoding a thermostable polymerase. Because there may not be an exact match between the nucleotide sequence of the thermostable DNA polymerase gene of Pab and Poc and the corresponding gene of other species, oligomers containing approximately 12–18 nucleotides (encoding the four to six amino acid sequence) are usually necessary to obtain hybridization under conditions of sufficient stringency to eliminate false positives. Sequences encoding six amino acids supply ample information for such probes.

The present invention, by providing the coding and amino acid sequences for Pab and Poc DNA polymerases, therefore enables the isolation of other thermostable polymerase enzymes and the coding sequences for those enzymes. Specifically, the invention provides means for preparing primers and probes for identifying nucleic acids encoding DNA polymerase enzymes contained within DNA isolates from related archaebacteria such as extreme hyperthermophiles including additional Pyrodictium species, *P. brockii*, and Methanopyrus species such as *M. kandleri*.

Several such regions of similarity between the Pab and Poc DNA polymerase coding sequences exist. For regions nine codons in length, probes corresponding to these regions can be used to identify and isolate sequences encoding thermostable polymerase enzymes that are identical (and complementary) to the probe for a contiguous sequence of at least five codons. For the region six codons in length, a probe corresponding to this region can be used to identify and isolate thermostable polymerase-encoding DNA sequences that are identical to the probe for a contiguous sequence of at least four codons.

One property found in the Pyrodictium DNA polymerase enzymes, but lacking in native Taq DNA polymerase and native Tth DNA polymerase, is 3'→5' exonuclease activity. This 3'→5' exonuclease activity is generally considered to be desirable, because misincorporated or unmatched bases of the synthesized nucleic acid sequence are eliminated by this activity. Therefore, the fidelity of PCR utilizing a polymerase with 3'→5' exonuclease activity (e.g. Pyrodictium DNA polymerase enzymes) is increased. However, the 3'→5' exonuclease activity found in Pyrodictium DNA polymerase enzymes can also increase non-specific background amplification in PCR by modifying the 3' end of the primers. The 3'→5' exonuclease activity can eliminate single-stranded DNAs, such as primers or single-stranded template. In essence, every 3'-nucleotide of a single-stranded primer or template is treated by the enzyme as unmatched and is therefore degraded. To avoid primer degradation in PCR, one can add phosphorothioate to the 3' ends of the primers. Phosphorothioate modified nucleotides are more resistant to removal by 3'→5' exonucleases.

Whether one desires to produce an enzyme identical to native Pab or Poc DNA polymerase or a derivative or homologue of that enzyme, the production of a recombinant form of the polymerase typically involves the construction of an expression vector, the transformation of a host cell with the vector, and culture of the transformed host cell under conditions such that expression will occur. To construct the expression vector, a DNA is obtained that encodes the mature (used here to include all muteins) enzyme or a fusion of the polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant Pyrodictium polymerase. The Pyrodictium polymerase is isolated from the medium or from the cells; recovery and purification of the protein may not be necessary in some instances, where some impurities may be tolerated.

Construction of suitable vectors containing the desired coding and control sequences employs standard ligation and restriction techniques that are well understood in the art (see, for example, *Molecular Cloning Laboratory Manual* 2nd ed., Sambrook et al., 1989, Cold Spring Harbor Press, New York, N.Y., which is incorporated herein by reference). Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector by methods well known in the art.

For portions of vectors or coding sequences that require sequence modifications, a variety site-specific primer-directed mutagenesis methods are available. For example, the polymerase chain reaction (PCR) can be used to perform site-specific mutagenesis. PCR Protocols, ed. by Innis et al., 1990, Academic Press, San Diego, Calif., and PCR Technology ed. by Henry Erlich, 1989, Stockton Press, New York, N.Y., describe methods for cloning, modifying, and sequencing DNA using PCR and are incorporated herein by reference.

Control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are, therefore, preferred for the expression of Pyrodictium DNA polymerase enzymes.

The procaryote most frequently used to express recombinant proteins is *E. coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ control sequence, *E. coli* K12 strain MC1000 lambda lysogen, $N_7 N_{53} cI857 SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of Pyrodictium DNA polymerase enzymes.

In addition to bacteria, eucaryotic microbes, such as yeast, can also be used as recombinant host cells. See, for example, Stinchcomb et al., 1979, *Nature* 282:39; Tschempe et al., 1980, *Gene* 10:157; and Clarke et al., 1983, *Meth. Enz.* 101:300.

The Pyrodictium gene can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Plant cells can also be used as hosts, and control sequences compatible with plant cells, such as the nopaline synthase promoter and polyadenylation signal sequences (Depicker et al., 1982, *J. Mol. Appl. Gen.* 1:561) are available.

Depending on the host cell used, transformation is done using standard techniques appropriate to such cells. The calcium treatment employing calcium chloride, as described by Cohen, 1972, *Proc. Natl. Acad. Sci. U.S.A.* 69:2110 is used for procaryotes or other cells that contain substantial cell wall barriers. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946 and Hsiao et al., 1979, *Proc. Natl. Acad. Sci. U.S.A.* 76:3829.

Once the Pyrodictium DNA polymerase has been expressed in a recombinant host cell, purification of the protein may be desired. Although the purification procedures previously described can be used to purify the recombinant thermostable polymerase of the invention, hydrophobic interaction chromatography purification methods are preferred. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, e.g., high ionic strength. A descending salt gradient may be used to elute the sample.

Detailed protocols for purifying recombinant thermostable DNA polymerases have been described in, for example, PCT Patent Publication Nos. WO 92/03556, published Mar. 5, 1992, and WO 91/09950, published Jul. 11, 1991. These publications are incorporated herein by reference. The methods described therein for *Thermotoga maritima* are suitable. Example 9 provides a preferred protocol for purifying recombinant Pyrodictium polymerase enzymes.

For long-term stability, the Pyrodictium DNA polymerase enzyme is preferably stored in a buffer that contains one or more non-ionic polymeric detergents. Such detergents are generally those that have a molecular weight in the range of approximately 100 to 250,00 preferably about 4,000 to 200,000 daltons and stabilize the enzyme at a pH of from about 3.5 to about 9.5, preferably from about 4 to 8.5. Examples of such detergents include those specified on pages 295–298 of McCutcheon's *Emulsifiers & Detergents*, North American edition (1983), published by the McCutcheon Division of MC Publishing Co., 175 Rock Road, Glen Rock, N.J. (U.S.A.), the entire disclosure of which is incorporated herein by reference. Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, Del., and Iconol™ NP-40, an ethoxylated alkyl phenol (nonyl) from BASF Wyandotte Corp. Parsippany, N.J.

The thermostable enzyme of this invention may be used for any purpose in which such enzyme activity is necessary or desired. In a particularly preferred embodiment, the enzyme catalyzes the nucleic acid amplification reaction known as PCR.

Although the PCR process is well known in the art (sec U.S. Pat. Nos. 4,683,195; 4,683,202; and 4,965,188, each of which is incorporated herein by reference) and although commercial vendors, such as Perkin Elmer, sell PCR reagents and publish PCR protocols, some general PCR information is provided below for purposes of clarity and full understanding of the invention to those unfamiliar with the PCR process.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples arc known in the art. For example, see those described in Higuchi et al., 1989 in PCR Technology (Erlich ed., Stockton Press, New York).

Because the nucleic acid in the sample is first denatured (assuming the sample nucleic acid is double-stranded) to begin the PCR process, and because simply heating some samples results in the disruption of cells, isolation of nucleic acid from the sample can sometimes be accomplished in conjunction with strand separation. Strand separation can be accomplished by any suitable denaturing method, however, including physical, chemical, or enzymatic means. Typical heat denaturation involves temperatures ranging from about 80°–105° C. for times ranging from seconds to about 1 to 10 minutes.

As noted above strand separation may be accomplished in conjunction with the isolation of the sample nucleic acid or as a separate step. In the preferred embodiment of the PCR process, strand separation is achieved by heating the reaction to a sufficiently high temperature for an effective time to cause the denaturation of the duplex, but not to cause an irreversible denaturation of the polymerase (see U.S. Pat. No. 4,965,188). No matter how strand separation is achieved, however, once the strands are separated, the next step in PCR involves hybridizing the separated strands with primers that flank the target sequence. The primers are then extended to form complementary copies of the target strands, and the cycle of denaturation, hybridization, and extension is repeated as many times as necessary to obtain the desired amount of amplified nucleic acid.

For successful PCR amplification, the primers are designed so that the position at which each primer hybridizes along a duplex sequence is such that an extension product synthesized from one primer, when separated from the template (complement), serves as a template for the extension of the other primer to yield an amplified segment of nucleic acid of defined length.

Template-dependent extension of primers in PCR is catalyzed by a polymerizing agent in the presence of adequate amounts of four deoxyribonucleoside triphosphates (dATP, dGTP, dCTP, and dTrP) in a reaction medium comprised of the appropriate salts, metal cations, and pH buffering system.

The amplification method is useful not only for producing large amounts of a specific nucleic acid sequence of known sequence but also for producing nucleic acid sequences which are known to exist but are not completely specified. One need know only a sufficient number of bases at both ends of the sequence in sufficient detail so that two oligonucleotide primers can be prepared which will hybridize to different strands of the desired sequence at relative positions along the sequence such that an extension product synthesized from one primer, when separated from the template (complement), can serve as a template for extension of the other primer into a nucleic acid sequence of defined length. The greater the knowledge about the bases at both ends of the sequence, the greater can be the specificity of the primers for the target nucleic acid sequence and the efficiency of the process.

Any nucleic acid sequence, in purified or nonpurified form, can be utilized as the starting nucleic acid(s), provided it contains or is suspected to contain the specific nucleic acid sequence desired. Thus, the process may employ, for example, DNA or RNA, including messenger RNA, which DNA or RNA may be single-stranded or double-stranded. For example, if the template is RNA, a suitable polymerizing agent to convert the RNA into a complementary, copy-DNA (cDNA) sequence is reverse transcriptase (RT), such as avian myeloblastosis virus RT and *Thermus thermophilus* DNA polymerase, a thermostable DNA polymerase with reverse transcriptase activity developed and manufactured by Hoffmann-La Roche Inc. and marketed by Perkin Elmer.

Whether the nucleic acid is single- or double-stranded, the DNA polymerase from Pyrodictium may be added at the denaturation step or when the temperature is being reduced to or is in the range for promoting hybridization. Although the thermostability of Pyrodictium polymerase allows one to add the polymerase to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80°–90° C.).

Depending on the nucleic acid(s) employed, the typical temperature effective for this synthesis reaction generally ranges from about 40°–80° C., preferably 50°–75° C. The temperature more preferably ranges from about 65°–75° C. for *P. occultum* and *P. abyssi* DNA polymerase enzymes. The period of time required for this synthesis may range from about 0.5 to 40 minutes or more, depending mainly on the temperature, the length of the nucleic acid and the enzyme. The extension time is usually about 30 seconds to three minutes. If the nucleic acid is longer, a longer time period is generally required for complementary strand synthesis.

Those skilled in the art will know that the PCR process is most usually carded out as an automated process with a thermostable enzyme. In this process, the temperature of the reaction mixture is cycled through a denaturing region, a primer annealing region, and a reaction region. A machine specifically adapted for use with a thermostable enzyme is commercially available from Perkin Elmer.

Those skilled in the art will also be aware of the problem of contamination of a PCR by the amplified nucleic acid from previous reactions. Methods to reduce this problem are provided in U.S. patent application Ser. No. 609,157, filed Nov. 2, 1990 now abandoned, incorporated herein by reference.

PCR amplification may yield primer dimers or oligomers, double-stranded side products containing the sequences of several primer molecule joined end-to-end, the yield of which correlates negatively with the yield of amplified target sequence. Nonspecific priming and primer dimer and oligomer formation can occur whenever all of the PCR reagents are mixed, even at ambient and sub-ambient temperatures in the absence of thermal cycling and in the presence or absence of target DNA. At 37° C., for example, Taq retains approximate 1–2% activity, although the optimal temperature is about 75°–80° C. Methods for overcoming non-specific extension and primer dimer formation include segregation of at least one reagent from the others in a way such that all reagents do not come together before the first amplification cycle. PCT Patent Publication No. WO 91/12342, which is incorporated herein by reference, describes methods and compositions for minimizing non-specific extension and primer dimer.

Because of the extremely high optimum growth temperature of Pyrodictium species, the present invention provides compositions that may be useful for minimizing non-specific primer extension. Specifically, the optimal growth temperature for *Pyrodictium occultum* and *P. abyssi* is 100°–105° C., approximately 30°–35° C. higher than, for example, *Thermus aquaticus*. Consequently, the residual activity of Pyrodictium DNA polymerases at room temperature is expected to be minimal and may eliminate the need to segregate at least one reagent prior to the first cycle of PCR. Thus, the present invention offers the potential of reduced non-specific extension at non-stringent annealing temperatures in a PCR without the use of wax barriers or other means of reagent segregation.

Those of skill in the art will recognize that the present invention provides novel compositions for the practice of any methods for which a DNA polymerase has utility. In a preferred embodiment, the enzymes are useful for amplifying nucleic acid sequences by PCR. Other amplification methods, particularly those requiring a heat denaturation step such as PLCR (Barany, 1991, *PCR Methods and Applications* 1(1):5–13) or gap-LCR (see, for example, PCT Patent Publication No. 90/01069, published Feb. 8, 1990) will also benefit from the present invention. Cycle sequencing methods (Caruthers et al., 1989, *BioTechniques* 7:494–499, and Koop et al., 1992, *BioTechniques* 14:442–447, incorporated herein by reference) will particularly benefit from 3'-5' exonuclease deficient Pab and Poc DNA polymerase enzymes.

Pyrodictium DNA polymerase is very useful in carrying out the diverse processes in which amplification of a nucleic acid sequence by the polymerase chain reaction is useful. Such methods include cloning, DNA sequencing, reverse transcription and asymmetric PCR. Further, the enzymes of the invention are suitable for use in diagnostic, forensic, and research applications. The following examples are offered by way of illustration only and by no means intended to limit the scope of the claimed invention.

EXAMPLE 1

Construction of a Genomic Pyrodictium Abyssi
DNA Library and Identification of the Pab
Polymerase Gene by a Colony Blot Thermostable
DNA Polymerase Activity Assay

*Pyrodictium abyssi* cells were received from Dr. Karl O. Stetter, University Regensburg, Regensburg, Germany. The isolate, AVZ (DSM6158) is described in Pley et al., 1991, System Applied Microbiology 14:245–253, which is incorporated herein by reference. DNA was purified by the method described in Lawyer et al., 1989, *J. Biological Chemistry* 264(11):6427–6437, which is incorporated herein by reference. About 25 µg of *Pyrodictium abyssi* DNA was partially digested with the restriction enzyme Sau3AI and size-fractionated by gel electrophoresis. Ten ng of fragments which were larger than 3.5 kb and smaller than 8.5 kb were used for cloning into the BamHI site of pUC19 vector (Clontech, Palo Alto, Calif.). The pUC19 plasmid vector has the lac promoter upstream from the BamHI cloning site. The promoter can induce heterologous expression of cloned open reading frames lacking promoter sequences. The recombinant plasmids were transformed into *E. coli* SURE cells (Strategene). Genotype of SURE® cells: mcrA, Δ (mcrBC-hsdRMS-mrr) 171, endA1, supE44, thi-1, λ-, gyrA96, relA1, lac, recB, recJ, sbcC, umuC::Tn5(kan$^R$), urvC, (F', proAB, lacI ZΔM15, Tn10[tet$^R$]).

A rapid filter assay for the detection of thermoresistant and thermophilic DNA polymerase activity was used to screen the *Pyrodictium abyssi* genomic DNA library (Sagner et al., 1991, *Gene* 97:119–123, incorporated herein by reference). According to the method, recombinant colonies are bound to nitrocellulose membrane and are incubated at elevated temperature in a polymerization buffer containing α[$^{32}$P]-labeled dNTPs. By autoradiography of the dried filters, colonies which express thermophilic DNA polymerase activity can be directly identified. The membrane-bound colonies are heated to 95° C. to irreversibly inactivate host DNA polymerases and are subsequently incubated at elevated temperatures to reveal the presence of thermophilic DNA polymerase activity.

Approximately 500 colonies were plated per petri dish and grown overnight at 37° C. Subsequently, the colonies were replica-plated onto nitrocellulose membranes and grown for 4 hours. The membranes were placed upside down on agarose plates which were placed for 20 minutes at room temperature on filter papers soaked with a mixture of chloroform/toulene (1:1). The membranes containing the permeabilized colonies were then incubated at 95° C. for 5 minutes in a polymerization buffer containing 50 mM Tris-HCl pH 8.8, 7 mM MgCl$_2$, 3 mM βMe to inactivate any nonthermoresistant (e.g., *E. coli*) DNA polymerase activity. Immediately after inactivation the membranes were transferred to the polymerization buffer containing 50 mM Tris-HCl pH 8.8, 7 mM MgCl$_2$, 3 mM βMe, 12 μM dCTP, 12 μM dGTP, 12 μM dATP, 12 μM dTTP, and 1 μCi per ml α[$^{32}$P]-dGTP. After incubation for 30 minutes at 65° C. the membranes were washed twice for 5 minutes in a solution of 5% TCA and 1% pyrophosphate to remove unincorporated α[$^{32}$P]-dGTP. The membranes were analyzed by autoradiography at −70° C. Seven clones were apparent on X-ray films of duplicated membranes after 3 days.

Plasmid DNAs were isolated from these 7 clones, restriction analysis was performed to determine the size and orientation of insert fragments relative to the pUC19 vector. DNA sequence analysis was performed on the largest clone, pPab 14. The "universal" forward and reverse sequencing primers, Nos. 1212 and 1233, respectively, purchased from New England BioLabs, Beverly, Mass., were used to obtain preliminary DNA sequences. From the preliminary DNA sequence, further sequencing primers were designed to obtain DNA sequence of more internal regions of the cloned insert. DNA sequence analysis has been performed for both strands.

EXAMPLE 2

Expression of the Pab Polymerase Gene

Plasmid pDG 168 is a λP$_L$ cloning and expression vector that comprises the λP$_L$ promoter and gene N ribosome-binding site (see, U.S. Pat. No. 4,711,845, which is incorporated herein by reference), a restriction site polylinker positioned so that the sequences cloned in to the polylinker can be expressed under control of the λP$_L$-N$_{RBS}$, and a transcription terminator form the *Bacillus thuringiensis* delta-toxin gene (see, U.S. Pat. No. 4,666,848, which is incorporated herein by reference). Plasmid pDG 168 also carries a mutated RNA II gene which renders the plasmid temperature sensitive for copy number (see, U.S. Pat. No. 4,631,257, which is incorporated herein by reference) and an ampicillin resistance gene in *E. coli* K12 strain DG 116. The construction of pDG168 is described in PCT Patent Publication No. WO 91/09950, published Jul. 11, 1991, at Example 6, which is incorporated herein by reference.

These elements act in concert to provide a useful and powerful expression vector. At 30°–32° C., the copy number of the plasmid is low, and in a host cell that carries a temperature sensitive λ repressor gene, such as cI857 the P$_L$ promoter does not function. At 37°–41° C., however, the copy number of the plasmid is 25–50 fold higher than at 30°–32° C., and the cI857 repressor is inactivated allowing the promoter to function. thus, pDG168 was selected for constructing expression vectors for Pab DNA polymerase.

The DNA sequence analysis of pPab14 revealed an open reading frame of 803 amino acids having an ATG start codon at nucleotide position 869 and a TGA stop codon at nucleotide position 3280. The 5' end of the Pab gene was mutagenized with oligonucleotide primers AW397 (SEQ ID No. 5) and AW398 (SEQ ID No. 6) by PCR amplification (as described below). AW397 (SEQ ID No. 5) is forward primer which was designed to alter the Pab DNA sequence at the ATG start to introduce an NdeI restriction site. Primer AW397 (SEQ ID No. 5) also introduced mutations in the fifth and sixth codons of the Pab polymerase gene sequence to be more compatible with the codon usage of *E. coli*, without changing the amino acid sequence of the encoded protein. The reverse primer, AW398 (SEQ ID No. 6), was chosen to include a SpeI site corresponding to amino acid position 174. In addition, a KpnI site was introduced after the SpeI site.

The PCR reaction mixture contained 10 ng of SalI linearized pPab14 DNA as the template; 10 pmol of primers AW397 (SEQ ID No. 5) and AW398 (SEQ ID No. 6); 50 μM of each dATP, dCTP, dTTP, and dGTP; 2 mM MgCl$_2$; 10 mM Tris-HCl, pH 8.3; 50 mM KCl and 1 unit Taq polymerase in 50 μgl reaction volume. The reaction thermoprofile was 95° C. for 30"; 65° C. for 30' and 72° C. for 30" and amplified for 12 cycles. The 500 bp amplified product was digested with NdeI and KpnI and loaded on an 1% Seakem agarose gel. The PCR product fragment was purified with Geneclean kit (Bio 101, San Diego, Calif.) and subcloned into expression vector pDG 168, which had been digested with NdeI and KpnI. The resulting clone was named pAW111. The desired mutations were confirmed via restriction enzyme analysis and DNA sequence analysis.

The 3' end of the Pab polymerase gene was modified via restriction enzyme digestion and use of a synthetic oligonucleotide duplex. AW399 (SEQ ID No. 7) was designed according to the 3' end of the Pab pol gene from AflII site at amino acid position 785–786. It changes the TGA stop codon to TAA as well. AW400 (SEQ ID No. 8) is the complementary strand of AW399 (SEQ ID No. 7) except that it has XmaI cohesive end at it's 5' end. When AW399 (SEQ ID No. 7) anneals to AW400 (SEQ ID No. 8), it produces a 60 bp synthetic duplex with 5' cohesive AflII/XmaI ends. The duplex was then cloned into plasmid pPab2 that have been digested with AlfII and XmaI. The resulting plasmid was designated pAW113. Plasmid Pab2 was one of the 7 clones isolated from the genomic library as described in Example 1. Plasmid Pab2 contains the entire Pab pol gene but is ~250 bp shorter than Pab14 at the 5' end. Thus, it lacks a flanking 5'-end AlfII site which facilitated the cloning strategy of replacing the 3' end AflII-XmaI fragment with the synthetic duplex AW399 (SEQ ID No. 7)/AW400 (SEQ ID No. 8) as described above. The DNA sequence of the replaced fragment was confirmed by DNA sequence analysis.

Finally, the 1.89 kb fragment of the Pab polymerase gene region, SpeI through the stop codon was isolated from pAW113 by digestion with SpeI and XmaI, and purified via gel electrophoresis. The resulting fragment was ligated with plasmid pAW111 that had been digested with SpeI and XmaI.

The ligation condition was 20 µg/ml DNA, 20 mM Tris-HCl, pH 7.4, 50 mM NaCl, 10 mM $MgCl_2$, 40 µM ATP and 0.2 Weiss unit T4 DNA ligase per 20 µl reaction at 16° C. overnight. Ligations were transformed into DG116 host cells. Candidates were screened for appropriate restriction enzyme sites. The desired plasmid was designated pAW115.

The oligonucleotides used in this example are shown below.

| AW397 | SEQ ID No. 5 | 5'GGACCCATATGCCAGAAGCTATTGAATTCGTGCTCC |
| AW398 | SEQ ID No. 6 | 5'GGCAGGTACCACTAGTTATGTCGGCAATAGGCTC |
| AW399 | SEQ ID No. 7 | 5'TTAAGGCAGCATCATCTGGGCATAGGAGTCT-CTTCGACTTCTTCGCGGCAAAGAAGTAAC |
| AW400 | SEQ ID No. 8 | 5'CCGGGTTACTTCTTTGCCGCGAAGAAGTCGAAGAGACT-CCTATGCCCAGATGATGCTGCC |

EXAMPLE 3

Cloning the Pyrodictium Occultum (Poc) DNA Polymerase Gene

Pab and Poc genomic DNA (0.5 µg each) were digested with HindIII, and were separated by gel electrophoresis through an 0.8% agarose gel. *Pyrodictium occultum* cells were received from Dr. Karl O. Stetter, University Regensburg, Regensburg, Germany. DNA was purified by the method described in Lawyer et al., 1989, *J. Biological Chemistry* 264(11):6427–6437, which is incorporated herein by reference. The DNA fragments in the gel were denatured in 1.5 M NaCl and 0.5 M NaOH solution for 30 minutes and were neutralized in a solution of 1 M Tris-HCl, pH 8.0 and 1.5 M NaCl for 30 minutes, and then were transferred to a Biodyne nylon membrane (Pall Biosupport, East Hills, N.Y.) using 20×SSPE (3.6 M NaCl, 200 mM $NaPO_4$/pH 7.4, 20 mM EDTA/pH 7.4). The DNA attached to the membrane was then hybridized to a $^{32}$P-labeled 240 bp PCR product which encoded amino acids 515–614 of the Pab polymerase gene. The prehybridization solution was 6×SSPE, 5× Denhardt's reagent, 0.5% SDS, 100 µg/ml denatured, sheared, salmon sperm DNA. Hybridization solution was the same except that Denhardt's reagent was used at 2×, and contained $10^6$ cpm $^{32}$P-labeled PCR-amplified probe. Prehybridization and hybridization were both at 55° C. The blot was washed sequentially as follows: 2×SSPE, 0.5% SDS, 10 minutes at RT; 2×SSPE, 0.1% SDS, 15 minutes at RT; 0.1% SSPE, 0.1% SDS, 5 minutes at RT.

A strong signal was apparent at approximately 3.8 kb in the HindIII digest. This suggested that the Poc polymerase gene has homology with the Pab polymerase gene. Consequently, several PCR primers, designed from the Pab polymerase gene sequence, were evaluated for amplification of portions of the Poc polymerase gene. A specific PCR product, 295 bp in size resulted from a PCR using primer pair LS417 (SEQ ID No. 34) and LS396 (SEQ ID No. 35).

| LS417 | SEQ ID No. 34 | 5'-GATAAAGATAGACAAGGTATAC |
| LS396 | SEQ ID No. 35 | 5'-CGTATTCCTCGATTCTCTTT |
| AW394 | SEQ ID No. 9 | 5'-GCTTATAGCCTTGTCCACGTTC |

The PCR was performed at final concentration of 1× PCR buffer, 50 gM dNTPs, 0.1 µM each primers, 1.25 units Taq in a total volume of 50 µl. 1× PCR buffer contains 20 mM Tris pH 8.4, 50 mM KCl, 2 mM $MgCl_2$. The reaction was amplified for 35 cycles.

The 295 bp PCR product was then subjected to DNA sequence analysis. The DNA sequence result showed that the Poc polymerase gene has 78% identity with the Pab polymerase gene in this region. A Poc polymerase specific oligonucleotide probe AW394 (SEQ ID No. 9) was designed using this DNA sequence data. The $^{32}$P-labeled AW394 (SEQ ID No. 9) was then used to screen a genomic Poc DNA bank to obtain Poc polymerase clones. The constriction of the genomic Poc DNA bank was as described in Example 1 for the genomic Pab DNA bank.

About 5,500 ampicillin-resistant colonies were selected on nitrocellulose filters and hybridized with $^{32}$P-labeled AW394 (SEQ ID No. 9). Plasmid DNA was isolated from 6 colonies that hybridized with the probe. Prehybridization and hybridization conditions were as described above. Wash conditions were 6×SSPE, 0.1% SDS for 5 minutes at room temperature and followed by 2×SSPE, 0.1% SDS for 15 minutes at 55° C. Restriction enzyme analysis and PCR analysis were performed to determine the size and orientation of insert fragment relative to the pUC19 vector. The results revealed that pPoc3 and pPoc5 are identical clones. The sizes of the coding region, 5' end non-translated region and 3' end non-translated region of all identified POc polymerase clones are listed below.

| Coding Region | 5'-end | 3'-end |
| --- | --- | --- |
| pPoc1 | 1.9 kb | 0 | 3.6 kb |
| pPoc2 | 1.9 kb | 0 | 4.2 kb |
| pPoc4 | 2.4 kb | 0.4 kb | 0.7 kb |
| pPoc5 | 0.35 kb | 0 | 4.5 kb |
| pPoc6 | 0.35 kb | 0 | 3.2 kb |
| pPoc8 | 0.7 kb | 3 kb | 0 |

DNA sequence analysis was performed on pPoc4. Universal and reverse sequencing primers were used to obtain preliminary DNA sequence information. From this DNA sequence additional sequencing primers were designed to obtain the DNA sequence of more internal regions of the insert. DNA sequence analysis has been performed for both strands.

EXAMPLE 4

Expression of the Poc Polymerase Gene

The 5' end of the Poc polymerase gene in plasmid pPoc4 was mutagenized with oligonucleotide primers AW408 (SEQ ID No. 10) and AW409A (SEQ ID No. 11) via PCR amplification. AW408 (SEQ ID No. 10) is a forward primer designed to alter the DNA sequence of the Poc gene at the ATG start codon to introduce an NsiI restriction site. AW408 (SEQ ID No. 10) also was designed to introduce alterations in the second, third, fifth, and sixth codons of the Poc gene to provide a sequence more compatible with the codon usage of E. coli without changing the amino acid sequence of the encoded protein. The reverse primer AW409A (SEQ ID No. 11) was chosen to include an XbaI site at amino acid position 38. In addition, a KpnI site was introduced after the XbaI site for subsequent subcloning.

Plasmid pPoc4, linearized with KpnI, was used as the PCR template for amplification using the AW408 (SEQ ID No. 10)/AW409A (SEQ ID No. 11) primer pair, yielding a 138 bp PCR product. The PCR amplification procedure was as described above at Example 2. The amplified fragment was digested with NsiI, then treated with Klenow to cream a blunt end at the NsiI-cleaved end, and finally digested with KpnI. The resulting fragment was ligated with expression vector pDG 164 (which is described in detail in PCT Patent Publication No. WO 91/09950, at Example 6b, and incorporated herein by reference) that has been digested with NdeI, repaired with Klenow, to fill in the overhang and provide a blunt end for ligation, and then digested with KpnI. The ligation yielded an in-frame coding sequence of the 5' end of the Poc polymerase gene under control of the $\lambda P_L$ promoter and bacteriophage $T_7$ gene 10 ribosome binding site. The resulting construct was designated pAW118.

was replaced by a Trp promoter sequences which was generated by PCR amplification using plasmid pLSG10 (plasmid pLSG10 is described in U.S. Pat. No. 5,079,352, which is incorporated herein by reference), as template and AW500 (SEQ ID No. 14) and AW501 (SEQ ID No. 15) as primers. The resulting PCR product was digested with NspV and NdeI and cloned into NspV and NdeI digested pAW115 to give rise to a Pab pol expression clone, pAW118, under control of the E. coli Trp promoter.

An internal NdeI site in the Poc pol gene of pAW121, complicates of the exchange NspV-NdeI $\lambda P_L$ promoter fragment and the Trp promoter fragment. Therefore, primers AW500 (SEQ ID No. 14) and AW502 (SEQ ID No. 16) were designed to amplify the Trp promoter sequence fragment from pLSG 10 and primers AW503 (SEQ ID No. 17) and AW504 (SEQ ID No. 18) were designed to amplify the 5' end 110 bp NdeI-XbaI fragment from pAW121. AW502 (SEQ ID No. 16) and AW503 (SEQ ID No. 17) overlap by 9 nucleotides. Using overlap extension PCR, the Trp promoter fragment and the 5' end 110 bp fragments were fused. The resulting PCR product was digested with NspV and XbaI and cloned into pAW121 which had been was digested with NspV and XbaI. The resulting Poc pol expression clone was named pAW123.

| AW500 | SEQ ID No. 14 | TTTTTCGAAAGAAGAAAAAACC |
| AW501 | SEQ ID No. 15 | TCTCATATGCTTATCGATACCC |
| AW502 | SEQ ID No. 16 | CATAAGCTTATCGATACCCTT |
| AW503 | SEQ ID No. 17 | AAGCTTATGACAGAGACTATAGAGTT |
| AW504 | SEQ ID No. 18 | GTGGTCTAGAAGCACGACACGT |

To effect subcloning of the 3' end of the Poc polymerase gene, a KpnI site was introduced after the stop codon. This was done by a PCR process as follows. The forward primer was chosen to include an EspI site at amino acid position 698–699, and the reverse primer was designed to incorporate a KpnI site immediately following an altered stop codon (TAA). The amplified 335 bp fragment was digested with EspI and KpnI, and cloned into plasmid pPoc4 digested with EspI and KpnI. The resulting construct was designated pAW120.

Finally, the Poc pol gene region XbaI through the stop codon was isolated from pAW120 by digestion with XbaI and KpnI. The resulting 2.3 kb fragment was ligated with pAW118 that had been digested with Xba and KpnI. The ligation product was transformed into DG116 host cells for expression and designated pAW121.

The oligonucleotides used in this example are given below.

EXAMPLE 6

Assessment of 3'-5' Exonuclease Activity: A Fidelity Assay

Because of the dramatic levels of amplification provided by the PCR process (up to $10^{11}$ to $6 \times 10^{12}$-fold), for certain applications the accuracy of replication (fidelity) is important. PCR fidelity is based on a two step process: misinsertion and misextension. If the DNA polymerase inserts an incorrect base and the resulting 3'-mismatched terminus is not extended, this truncated extension product cannot be amplified since the binding site for the downstream primer is not present. DNA polymerases extend a mismatched 3'-terminus more slowly than a matched 3'-terminus. In addition, different mismatches extend at disparate rates. See Kwok et al., 1990, *Nuc. Acids Res.* 18:999–1005, and Huang et al., 1992, *Nuc. Acids Res.* 20:4567–4573.

| AW408 | SEQ ID No. 10 | GGACCATGCATGACTGAAACTATTGAATTCGTGCTG |
| AW409A | SEQ ID No. 11 | GGAAGGTACCTGATCATCTAGAAGCACGACACGTT |
| AW410 | SEQ ID No. 12 | GGAAGCTGAGCAAGAGGATAGAGG |
| AW411A | SEQ ID No. 13 | GGAAGGTACCTTATTTCTTTGAGGCGAAGAAG |

EXAMPLE 5

Expression of Pab pol Gene and Poc pol Gene in Tryptophan Promoter Vector

Both the Pab pol gene and the Poc pol gene can be over-expressed under the control of the E. coli Trp promoter. Construction of the expression clones was performed as follows: The $\lambda P_L$ promoter in expression clone, pAW115, DNA polymerases with inherent 3' to 5' exonuclease or proofreading activity are able to improve fidelity by removing misinserted bases before extension. A convenient PCR and restriction endonuclease digestion assay has been developed to assess the ability of DNA polymerases with 3' to 5' exonuclease activity to remove 3'-terminal mismatched nucleotides prior to misextension. Several primers were designed which were either perfectly matched or 3'-mismatched (with every possible combination) to the first nucleotide of the BamHI restriction enzyme recognition sequence in the *Thermus aquaticus* DNA polymerase gene (Lawyer et al., 1989, *J. Biol. Chem.* 264:6427–6437 and U.S. Pat. No. 5,079,352). The perfect match primers, FR434 (SEQ ID No. 29) and FR438 (SEQ ID No. 33), amplify a 151 bp product that is completely digested with BamHI restriction enzyme to generate 132 bp and 19 bp DNA fragments. The 3'-terminal nucleotide of forward primer FR434 (SEQ ID No. 29) corresponds to nucleotide 1778 of the Taq DNA pol gene. Forward primers FR435 (SEQ ID No. 30), FR436 (SEQ ID No. 31), and FR437 (SEQ ID No. 32) contain a single 3'-terminal mismatch with respect to the wild-type Taq DNA pol gene and wild-type primer FR438 (SEQ ID No. 33) extension products, corresponding to A:C, T:C, and C:C mismatches, respectively. Any incorrect or misextension from primers FR435 (SEQ ID No. 30), FR436 (SEQ ID No. 31), or FR437 (SEQ ID No. 32) eliminates the BamHi recognition site corresponding to nucleotides 1778–1783 of the Taq DNA pol gene. Alternatively, exonucleolytic proofreading removes the 3'-terminal mismatched nucleotides and permits incorporation of the correct dG residue, resulting in the accumulation of PCR products that now contain the diagnostic BamHI restriction enzyme site. Since all of the FR435 (SEQ ID No. 30), FR436 (SEQ ID No. 31), or FR437 (SEQ ID No. 32) primers are mismatched to the original target, this PCR/endonuclease digestion assay requires exonucleolytic proofreading in every cycle to correct the "mutant" primers and generate a PCR product that contains the diagnostic BamHI cleavage site. Misextension at any cycle will generate an efficiently copied (now mutant) template in the succeeding cycle (from primer FR438 [SEQ ID No. 33] extension) that is perfectly matched to all of the primers in the assay.

| | | * |
|---|---|---|
| FR434 | SEQ ID No. 29 | 5'-GCACCCCGCTTGGGCAGAG |
| FR435 | SEQ ID No. 30 | 5'-GCACCCCGCTTGGGCAGAA |
| FR436 | SEQ ID No. 31 | 5'-GCACCCCGCTTGGGCAGAT |
| FR437 | SEQ ID No. 32 | 5'-GCACCCCGCTTGGGCAGAC |
| FR438 | SEQ ID No. 33 | 5'-TCCCGCCCCTCCTGGAAGAC |

Primer FR434 (SEQ ID No. 29) corresponds identically to nucleotides 1760 through 1778 of the Taq DNA polymerase gene, and primer FR438 (SEQ ID No. 33) is complementary to nucleotides 1891 through 1910 of the Taq DNA polymerase gene. Primers FR435 (SEQ ID No. 30), FR436 (SEQ ID No. 31), and FR437 (SEQ ID No. 32) correspond identically to nucleotides 1760 through 1777 of the Taq DNA polymerase gene and contain the indicated (by *, underlined) 3'-terminal mismatched nucleotide at position 1778.

Recombinant Pab and Poc DNA polymerases were purified from *E. coli* K12 strain DG116 harboring plasmids pAW115 or pAW121, respectively. The purification involved cell lysis, heat treatment at 75°–85° C., polymin P precipitation of bulk nucleic acids, phenyl sepharose chromatography and heparin sepharose chromatography, according to Example 9.

Using this fidelity assay, wild-type recombinant Pab and Poc DNA polymerases are able to correct mismatch primers FR435 (SEQ ID No. 30), FR436 (SEQ ID No. 31) and FR437 (SEQ ID No. 32) to generate PCR product that contains the requisite BamHI cleavage site, demonstrating the presence of 3' to 5' exonucleolytic proofreading activity.

EXAMPLE 7

Production of 3'-5' exonuclease mutants of Pab pol and Poc pol

Pab and Poc pol genes lacking 3'-5' exonuclease activity were constructed using site-directed mutagenesis by overlap extension PCR to alter the codons for Asp187 and Glu189 to code for alanine. Briefly, mutagenesis by overlap extension PCR involves the generation of DNA fragments that, by virtue of having incorporated complementary oligo primers in independent PCR reactions (see, Higuchi et al., 1988, *Nuc. Acids Res.* 16:7351–7367, and Ho et al., 1989, *Gene* 77:51–59, which are incorporated herein by reference, for a detailed description of this method). According to the method, these fragments are combined in a subsequent "fusion" reaction in which the overlapping ends anneal, allowing the 3' overlap of each strand to serve as a primer for the 3' extension of the complementary strand. The resulting fusion product is amplified further by PCR. Specific alterations in the nucleotide sequence can be introduced by incorporating nucleotide changes into the overlapping oligo primers.

The construction of a 3'–5' exonuclease minus mutant of Pab was accomplished as follows. The two overlapped primers AW493 (SEQ ID No. 20) and AW494 (SEQ ID No. 21) were designed to span Asp187 and Glu189, in which both Asp187 and Glu189 are replaced by alanine. The two external primers, AW492 (SEQ ID No. 19) and AW495 (SEQ ID No. 22), were chosen to locate at the unique SpeI and NsiI restriction sites at amino acid position 174–175 and amino acid position 304–305, respectively, thus making it possible to ligate the fusion product back into the expression vector. The products from the PCR using primer sets AW492 (SEQ ID No. 19)/AW493 (SEQ ID No. 20) and AW494 (SEQ ID No. 21)/AW495 (SEQ ID No. 22) were 70 bp and 373 bp fragments, respectively. The resulting two fragments (27 nucleotide 3' overlap) were fused by denaturing and annealing them in a subsequent primer extension reaction. The 416 bp fusion product was amplified further by PCR using the two external primers AW492 (SEQ ID No. 19) and AW495 (SEQ ID No. 22). The mutagenized 416 bp fragment was then cut with SpeI and NsiI and ligated back into the parent clone pAW115 which had also been digested with SpeI and NsiI. The resulting mutant clone was named pexo-Pab, and the desired mutations were confirmed by sequence analysis.

Similarly, the 3'–5' exonuclease minus mutant of Poc was constructed using the same approach. The overlapping primer pair used to introduce the mutation are AW489 (SEQ ID No. 24) and AW490 (SEQ ID No. 25). The two external primers, AW488 (SEQ ID No. 23) and AW491 (SEQ ID No. 26) are located at the unique XbaI and BssHII restriction sites at amino acid positions 37–39 and 260–262, respectively. The products from PCR using primer sets AW488 (SEQ ID No. 23)/AW489 (SEQ ID No. 24) and AW490 (SEQ ID No. 25)/AW491 (SEQ ID No. 26) were 476 bp and 243 bp fragments, respectively. These two fragments were fused and subjected to PCR amplification using the external primers AW488 (SEQ ID No. 23) and AW491 (SEQ ID No. 26). The mutagenized fragment was then cut with XbaI and BssHII and ligated back into the parent clone pAW121. The resulting mutant clone was named pexo-Poc.

The exonuclease activities of the exo-Pab DNA polymerase and exo-Poc DNA polymerase were determined using the mismatch incorporation proofreading assay. The results showed that both the exo-Pab pol and exo-Poc pol lacked the 3'–5' exonuclease activity.

| | | |
|---|---|---|
| AW492 | SEQ ID No. 19 | 5'-TATTGCCGACATAACTAGTATAGA |
| AW493 | SEQ ID No. 20 | 5'-ACTGTAGACCGCGATCGCGAACGCGAGC |
| AW494 | SEQ ID No. 21 | 5'-CTCGCGTTCGCGATCGCGGTCTACAGTAAGAGAG |
| AW495 | SEQ ID No. 22 | 5'-TTATCTCATGCATTTCCTCC |
| AW488 | SEQ ID No. 23 | 5'-GTGTCGTGCTTCTAGACCA |
| AW489 | SEQ ID No. 24 | 5'-GCTATACACCGCGATCGCAAAAGCTACCAGC |
| AW490 | SEQ ID No. 25 | 5'-GGTAGCTTTTGCGATCGCGGTGTATAGCAGGA |
| AW491 | SEQ ID No. 26 | 5'-TACGGGCGCGCTCCATTAG |

EXAMPLE 8

Thermostability comparison of Pab pol, Poc pol and Taq pol in PCR

The upper growth temperature of hyperthermophilic genus Pyrodictium is 110° C. To test the thermostability of purified recombinant Pab pol, Poc pol and Taq pol in the PCR process, the following experiment was performed: 0.1 pg, 1 pg, and 10 pg of M13 DNA (New England Biolabs, Beverly, Mass.) were used as templates for PCR analysis by Pab, Poc and Taq. The reactions were subjected to 25, 30, 35 and 40 cycles at denaturing temperatures of 95° C. or 100° C. A PCR product of 350 bp was generated by using BW36 (SEQ ID No. 27) and BW42 (SEQ ID No. 28) as primers. BW36 SEQ ID No. 27 5'CCGATAGTTTGAGTTCTTC-TACTCAGGC BW42 SEQ ID No. 28 5'GAAGAAAGC-GAAAGGAGCGGGCGCTAGGGC PCR was performed at a final concentration of 1×PCR buffer, 50 μgM dNTPs, 0.1 μM each primers, 0.25 units Pab or 0.1 units Poc or 1.25 units Taq in a total reaction volume of 50 μl.

A unit of Pab DNA polymerase and a unit of PoC DNA polymerase is defined, like for Taq DNA polymerase, as the amount of enzyme that will incorporate 10 nmoles total dNTPs into acid insoluble material per 30 minutes at 74° C. Poc and Pab DNA polymerases are assayed as described in U.S. Pat. No. 4,889,818, which is incorporated herein by reference, for Taq DNA polymerase with the following changes in reaction components. Pab DNA polymerase: Tris-HCl pH 8.3 (25° C.), 100 mM KCl, 5 mM MgCl$_2$. Poc DNA polymerase: Tris-HCl pH 8.0 (25° C.), 10 mM KCl, 5 mM MgCl$_2$. 1×PCR buffer for Pab contains: 20 mM Tris-HCl, pH 8.4, 100 mM KCl, 1.5 mM MgCl$_2$. 1×PCR buffer for Poc contains: 20 mM Tris-HCl, pH 8.4, 10 mM KCl, 1.0 mM MgCl$_2$. 1×PCR buffer for Taq contains: 20 mM Tris, pH8.4, 50 mM KCl, 1.5 mM MgCl$_2$. The amplification profile involved denaturation at 95° C. or 100° C. for 30 seconds, primer annealing and extension at 55° C. for 30 seconds. The results showed that both Pab pol and Poc pol were extremely thermoresistant, functioning effectively in the PCR with denaturing temperature up to 100° C. In contrast, Taq pol produced no product under these conditions at 100° C.

EXAMPLE 9

Purification of Recombinant Pyrodictium DNA Polymerase

Recombinant Pyrodictium DNA polymerase is purified as follows. Briefly, cells are thawed in 1 volume of TE buffer (50 mM Tris-Cl, pH 7.5, and 1.0 mM EDTA with 1 mM DTT), and protease inhibitors are added (PMSF to 2.4 mM, leupeptin to 1 μg/ml, and TLCK to 0.2 mM). The cells are lysed in an Aminco french pressure cell at 20,000 psi and sonicated to reduce viscosity. The sonicate is diluted with TE buffer and protease inhibitors to 5.5× wet weight cell mass (Fraction I), adjusted to 0.2M ammonium sulfate, and brought rapidly to 85° C. and maintained at 85° C. for 15 minutes. The heat-treated supernatant is chilled rapidly to 0° C., and the E. coli cell membranes and denatured proteins are removed following centrifugation at 20,000×G for 30 minutes. The supernatant containing Pyrodictium DNA polymerase (Fraction II) is saved. The level of Polymin P necessary to precipitate >95% of the nucleic acids is determined by trial precipitation (usually in the range of 0.6 to 1% w/v). The desired amount of Polymin P is added slowly with rapid stirring at 0° C. for 30 minutes and the suspension centrifuged at 20,000×G for 30 min. to remove the precipitated nucleic acids. The supernatant (Fraction III) containing the Pyrodictium DNA polymerase is saved.

Fraction III is adjusted to 0.3 M ammonium sulfate and applied to a phenyl separose column that has been equilibrated in 50 mM Tris-Cl, pH 7.5, 0.3 M ammonium sulfate, 10 mM EDTA, and 1 mM DTT. The column is washed with 2 to 4 column volumes of the same buffer (A$_{280}$ to baseline), and then 1 to 2 column volumes of TE buffer containing 50 mM KCl to remove most contaminating E. coli proteins. Pyrodictium DNA polymerase is then eluted from the column with buffer containing 50 mM Tris-Cl, pH 7.5, 2 M urea, 20% (w/v) ethylene glycol, 10 mM EDTA, and 1 mM DTT, and fractions containing DNA polymerase activity are pooled (Fraction IV).

Final purification of recombinant Pyrodictium DNA polymerase is achieved using heparin sepharose chromatography, anion exchange chromatography, or affixed blue chromatography. Recombinant Pyrodictium DNA polymerase may be diafiltered into 2.5× storage buffer (50 mM Tris-HCl pH 8.0, 250 mM KCl, 2.5 mM DTT, 0.25 mM EDTA, 0.5% [w/v] Tween20), combined with 1.5 volumes of sterile 80% (w/v) glycerol, and stored at –20° C.

ATCC Deposits

The following bacteriophage and bacterial strains were deposited with the American Type Culture Collection, 12301 Parklawn Drive, Rockville, Md., U.S.A. (ATCC). These deposits were made under the provisions of the Budapest Treaty on the International Recognition of the Deposit of Microorganisms for purposes of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Applicants and ATCC that assures unrestricted availability upon issuance of the pertinent U.S. patent. Availability of the deposited strains is not to be construed as a license to practice the invention in contravention of the rights granted under the authority of any government in accordance with its patent laws.

| Deposit Designation | ATCC No. | Date of Deposit |
|---|---|---|
| pPab 14 | 69310 | 05/11/93 |
| pPoc 4 | 69309 | 05/11/93 |

The foregoing written specification is considered to be sufficient to enable one skilled in the an to practice the invention. The present invention is not to be limited in scope by the cell lines deposited, since the deposited embodiment is intended as a single illustration of one aspect of the invention and any cell lines that are functionally equivalent are within the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown are described herein will become apparent to those skilled in the art from the foregoing description and fall within the scope of the appended claims.

We claim:

1. A purified protein that consists of an amino acid sequence that is SEQ ID NO: 2 or SEQ ID NO: 4.

2. The purified protein of claim 1, wherein the amino acid sequence is SEQ ID NO: 2.

3. The purified protein of claim 1, wherein the amino acid sequence is SEQ ID NO: 4.

4. A purified DNA consisting of a sequence that encodes an amino acid sequence that is SEQ ID NO: 2 or SEQ ID NO: 4.

5. A DNA of claim 4 that encodes the amino acid sequence of SEQ ID NO: 2.

6. A DNA of claim 5 consisting of the nucleic acid sequence of SEQ ID NO: 1.

7. A DNA of claim 4 that encodes the amino acid sequence of SEQ ID NO: 4.

8. A DNA of claim 7 consisting of the nucleic acid sequence of SEQ ID NO: 3.

9. A recombinant DNA vector that comprises a DNA of claim 4.

10. A recombinant DNA vector that comprises a DNA of claim 6.

11. A recombinant DNA vector that comprises a DNA of claim 8.

12. A recombinant DNA vector of claim 9, selected from the group consisting of pAW121, pPoc4, pAW115, pPab14, pAW123, and pAW118.

13. A recombinant host cell transformed with a vector of claim 9.

14. A purified DNA polymerase that is encoded by pexo-Pab or pexo-Poc.

15. The purified protein of claim 14 that is encoded by pexo-Pab.

16. The purified protein of claim 14 that is encoded by pexo-Poc.

17. A purified DNA that encodes the DNA polymerase encoded by pexo-Pab or pexo-Poc.

18. A recombinant DNA vector that comprises the DNA sequence of claim 17.

19. A recombinant DNA vector of claim 18 that is pexo-Pab or pexo-Poc.

20. A recombinant host cell transformed with a vector of claim 19.

* * * * *